(12) United States Patent
Kondo et al.

(10) Patent No.: US 8,558,035 B2
(45) Date of Patent: Oct. 15, 2013

(54) REACTION PROCESS UTILIZING CRITICAL WATER

(75) Inventors: Takeyuki Kondo, Hitachi (JP); Hiroyuki Ito, Tokyo (JP); Naruyasu Okamoto, Tokyo (JP); Yasunari Sase, Tokyo (JP); Toshiaki Matsuo, Mito (JP); Kenichiro Oka, Mito (JP); Masayuki Kamikawa, Hitachinaka (JP)

(73) Assignee: Hitachi Plant Technologies, Ltd., Tokyo (JP)

( * ) Notice: Subject to any disclaimer, the term of this patent is extended or adjusted under 35 U.S.C. 154(b) by 18 days.

(21) Appl. No.: 13/148,760

(22) PCT Filed: Feb. 5, 2010

(86) PCT No.: PCT/JP2010/051693
§ 371 (c)(1),
(2), (4) Date: Aug. 10, 2011

(87) PCT Pub. No.: WO2010/092909
PCT Pub. Date: Aug. 19, 2010

(65) Prior Publication Data
US 2011/0319667 A1    Dec. 29, 2011

(30) Foreign Application Priority Data

Feb. 12, 2009  (JP) ................................. 2009-030234

(51) Int. Cl.
*C07C 45/52* (2006.01)
*B01J 19/00* (2006.01)

(52) U.S. Cl.
USPC .......................................... 568/886; 422/187

(58) Field of Classification Search
CPC .................... C07C 45/515; C07C 45/52; B01J 2219/00006
USPC .......................................... 568/486; 422/187
See application file for complete search history.

(56) References Cited

FOREIGN PATENT DOCUMENTS

| JP | 2000-279975 | 10/2000 |
|---|---|---|
| JP | 2000-279976 | 10/2000 |
| JP | 2007-137785 | 6/2007 |
| JP | 2008-88149 | 4/2008 |

OTHER PUBLICATIONS

Antal et al., "Heterolysis and Homolysis in Supercritical Water," Preprints of papers—American chemical society, Division of fuel chemistry, 1985, pp. 78-87, vol. 30(3).
Ramayya et al., "Acid-Catalyzed Dehydration of Alcohols in Supercritical Water," Fuel, 1987, pp. 1364-1371, vol. 66(10).
"Manufacturing, applications and economics of 1,3-PDO, PTT," CMC Co., Ltd., Planet Business Dept., 2000 .
Watanabe et al., "Acrolein Synthesis from Glycerol in Hot-Compressed Water," Bioresource Technology, 2007, pp. 1285-1290, vol. 98, Elsevier Ltd.
L. Ott et al., Catalytic dehydration of Glycerol in Sub- and Supercritical Water, A New Chemical Process for Acrolein Production, Green Chem., 2006, vol. 8, No. 2, pp. 214-220.
Chinese Office Action Appln. No. 201080006984.4 dated Apr. 22, 2013.

*Primary Examiner* — Sikarl Witherspoon
(74) *Attorney, Agent, or Firm* — Antonelli, Terry, Stout & Kraus, LLP.

(57) ABSTRACT

In order to perform organic synthesis process through action with supercritical water and acid stably while suppressing a trouble caused by a by-product, a method and an apparatus are provided, including the following steps. Water is supplied to high-pressure pumps (110) and (210) from water headers (101) and (201), and a pressure-reducing valve (324) is regulated to increase the pressure to 35 MPa. Temperatures of preheaters (120) and (220) and a heater (310) are increased until the reaction solution is at a temperature of 400° C. Acid (sulfuric acid) and an organic compound raw material (glycerin) are supplied from an acid header (203) and a raw-material header (203') for action with the supercritical water to obtain a reaction solution. The obtained reaction solution is cooled to 100 to 200° C. by first cooling (420) and a solid component included in the reaction solution is separated for removal from the reaction solution by a filter (320), and then the reaction solution is cooled to a temperature of about 100° C. or lower by second cooling (620) and pressure thereof is reduced (324). Further, the reaction solution is cooled by third cooling (720) and then a synthesized product (acrolein) is captured.

31 Claims, 43 Drawing Sheets

REACTION PROCESS UTILIZING CRITICAL WATER

TECHNICAL FIELD

The present invention relates to a method for synthesizing organic matter using supercritical water, and more particularly relates to a method and an apparatus that synthesize acrolein as a raw material of 1,3-propanediol from glycerin in the presence of hydrogen ions.

BACKGROUND ART

As a raw material of high-quality polyester fiber including polytrimethylen-terephthalate, the demand for 1,3-propanediol has increased in recent years. One of available methods for synthesizing 1,3-propanediol includes an acrolein hydration/hydrogenation method disclosed in Non-Patent Document 1. This method has been established as an industrial manufacturing method, where acrolein is obtained by synthesizing propylene as a petroleum raw material by air oxidation in the presence of a catalyst and such acrolein undergoes a hydration/hydrogenation reaction to manufacture 1,3-propanediol. However, with the sharp rise in oil price in recent years, the development of a synthesis method from a bio raw material has been demanded.

Although a method for chemically synthesizing 1,3-propanediol from a bio raw material has not been reported so far, a technique of synthesizing acrolein as a precursor is available, which is reported by Non-Patent Document 2, for example. Non-Patent Document 2 discloses a method of using glycerin as a bio raw material for a starting material to synthesize acrolein using supercritical water at 400° C. and 35 MPa. The technique has a feature in that protons from a very small amount of sulfuric acid added to supercritical water function as a promoter to accelerate a dehydration reaction of glycerin. According to this method, however, a mixture of tar and carbon particles is generated by heat decomposition as a by-product and such a by-product might block pipes and valves. To avoid such blockage, it is required in this reaction to use low concentration of raw materials so as to decrease the generation amount of the by-product. As a result, energy and cost used for the rise of temperature and pressure of water that are required per production volume become enormous, so that industrialization for mass production is difficult.

Patent Document 1 reports an exemplary supercritical reactor for removing solid particles such as salts. This technique is created based on the fact that while water has a high dielectric constant at ordinary temperatures and pressures and so has high solubility of salts, water in a supercritical condition tends to cause deposition of salts because of a decrease in dielectric constant. In this technique, in order to suppress the pipe blockage due to solid salts that are deposited beyond the solubility in supercritical water, a hydrocyclone is provided in a pipe for separation and capturing of solid matter. Conceivably, even such a technique has difficulty to be applied simply to a by-product as a target of the present invention. This is because the by-product contains high-viscosity and sticky tar and the adhesion of such a by-product to pipes and to a removal device for solid particles inhibits the operation of the apparatus.

The present inventors actually fabricated a prototype of a supercritical reactor illustrated in FIG. 1 of the same type as the apparatus described in Patent Document 1, and performed a synthesis experiment of acrolein under the conditions of glycerin concentration from 1.5% described in Non-Patent Document 2 to 15% ten times thereof. As a result, it was confirmed that while a very small amount of by-product was generated under the condition of low glycerin concentration of 1.5%, a large amount of by-product was generated in a reaction solution under the condition of high glycerin concentration of 15%, thus increasing the tendency of blockage at pipes, valves, and filters or at narrow sections such as a hydrocyclone. As the operation was continued, it was further confirmed that solid matter of the by-product adhered to valve bodies and valve seats, resulting in that the operation range of valve bodies was limited by wearing-out of the valve bodies and the valve seats, and it became difficult to control pressure precisely. It was further found that solid matter of the by-product accumulated at a lower part of a pipe, thus causing erosion of the pipe. Conceivably this resulted from the by-product particles having a large particle size and having adhesiveness because they were generated by agglomeration of carbon particles due to the adhesiveness of tar.

Non-Patent Document 1: Manufacturing, applications and economics of 1,3-PDO PTT, CMC Co. Ltd., Planet Business Dept., August 2000

Non-Patent Document 2: M. Watanabe, et al., Acrolein synthesis from glycerol in hot-compressed water, Bioresource Technology (Elsevier Ltd.) 98 (2007) pp. 1285-1290

Patent Document 1: JP Patent Application Publication No. 2000-279976 A

DISCLOSURE OF THE INVENTION

Problem to be Solved by the Invention

It is an object of the invention to provide a technique for, in a reaction process through action of a high-concentration raw material of an organic compound with supercritical water and acid for industrialization, enabling stable synthesis of organic matter while suppressing blockage or erosion of a pipe and equipment due to generation of a by-product.

Means for Solving the Problem

In order to fulfill the aforementioned object, a method for synthesizing organic matter of the present invention includes the steps of: cooling a reaction solution by first cooling to 100 to 200° C. that are temperatures stopping a main reaction and keeping a high-viscosity component such as tar included in the reaction solution in a sufficiently lowered viscosity state, the reaction solution being obtained through action of supercritical water and acid with an organic compound raw material; separating, from the reaction solution, a solid component included in the reaction solution for removal; and then cooling the reaction solution by second cooling to a temperature of about 100° C. or lower that is the boiling point of water or lower, where tar components in the reaction solution does not adhere to equipment, followed by reducing pressure.

An apparatus that synthesizes organic matter of the present invention includes a reactor including: a high-pressure pump that sends at least water; a preheater that heats the sent water to generate supercritical water; a high-pressure pump that sends a mixture aqueous solution of an organic compound raw material and acid; a preheater that pre-heats the sent mixture aqueous solution; a heater that keeps a reaction solution obtained by mixing the supercritical water and the mixture aqueous solution at a reaction temperature; and a pressure-reducing valve. Along a flow path of the reaction solution, a first cooler, a separation and removal device for solid matter, a second cooler, and a pressure-reducing valve are provided in this order to allow the reaction solution to pass therethrough and be discharged.

Effects of the Invention

According to the present invention, in a reaction process through action of a high-concentration organic compound with supercritical water and acid, the amount of a by-product generated can be reduced and a solid component such as carbon particles of the by-product can be separated for removal by making sticky and high-viscosity tar in the solid component in a low viscosity state. Thereby, malfunctions and erosion of equipment such as a pipe, a valve, a filter or a hydrocyclone can be prevented, and pressure can be controlled precisely.

In this process, in the first cooling after the completion of reaction, cooling water is directly mixed with the reaction solution for cooling, whereby the reaction can be stopped speedily, and therefore the effect can be further improved.

The process from reaction to separation for removal is performed in a vertical pipe separated by a valve. Thereby, a by-product uniformly flows down by gravity with respect to the circumferential direction of the pipe, thus preventing solid matter from accumulating at a bottom of the pipe, which is generated in the case of a horizontal system, and thus increasing the effect of reducing erosion at pipes and pressure-reducing valves.

After cooling the reaction solution, a solid component is separated, and therefore thermal degradation of a separator can be prevented. Further since the temperature of the reaction solution is reduced to the boiling point of water or lower while suppressing the adhesion of tar prior to the pressure-reduction operation, abrupt expansion of the volume of the reaction solution due to vaporization after the pressure reduction can be suppressed, and so the reactor can be improved in safety.

After pressure-reduction of the reaction solution, the reaction solution is finally cooled so as not to fall below the boiling point of a target reaction material. Therefore, energy efficiency for collection of a target material at a distillation step performed later can be improved. Further, two or more systems are provided for the process from the reactor to the separator, whereby alternate operation and alternate emission of by-product particles are enabled, so that continuous operability can be improved and maintenance thereof can be facilitated. Herein, since a preheater in a first-half stage of the reactor has a device size larger than that of a heater of the reaction pipe and the solution stays longer in the former, the preheater is shared among the systems, and the reaction pipe or later is branched into the plurality of systems, whereby facility cost can be reduced.

BRIEF DESCRIPTION OF THE DRAWINGS

FIG. 5-1 shows an example of synthesizing acrolein through action of supercritical water and acid with glycerin (partial view 1).

FIG. 5-2 shows an example of synthesizing acrolein through action of supercritical water and acid with glycerin (partial view 2).

FIG. 5-3 shows an example of synthesizing acrolein through action of supercritical water and acid with glycerin (partial view 3).

FIG. 6-1 shows an example of synthesizing acrolein through action of supercritical water and acid with glycerin (partial view 1).

FIG. 6-2 shows an example of synthesizing acrolein through action of supercritical water and acid with glycerin (partial view 2).

FIG. 6-3 shows an example of synthesizing acrolein through action of supercritical water and acid with glycerin (partial view 3).

FIG. 7-1 shows an example of synthesizing acrolein through action of supercritical water and acid with glycerin (partial view 1).

FIG. 7-2 shows an example of synthesizing acrolein through action of supercritical water and acid with glycerin (partial view 2).

FIG. 7-3 shows an example of synthesizing acrolein through action of supercritical water and acid with glycerin (partial view 3).

FIG. 8-1 shows an example of synthesizing acrolein through action of supercritical water and acid with glycerin (partial view 1).

FIG. 8-2 shows an example of synthesizing acrolein through action of supercritical water and acid with glycerin (partial view 2).

FIG. 8-3 shows an example of synthesizing acrolein through action of supercritical water and acid with glycerin (partial view 3).

FIG. 9-1 shows an example of synthesizing acrolein through action of supercritical water and acid with glycerin (partial view 1).

FIG. 9-2 shows an example of synthesizing acrolein through action of supercritical water and acid with glycerin (partial view 2).

FIG. 9-3 shows an example of synthesizing acrolein through action of supercritical water and acid with glycerin (partial view 3).

FIG. 10-1 shows an example of synthesizing acrolein through action of supercritical water and acid with glycerin (partial view 1).

FIG. 10-2 shows an example of synthesizing acrolein through action of supercritical water and acid with glycerin (partial view 2).

FIG. 10-3 shows an example of synthesizing acrolein through action of supercritical water and acid with glycerin (partial view 3).

FIG. 11-1 shows an example of synthesizing acrolein through action of supercritical water and acid with glycerin (partial view 1).

FIG. 11-2 shows an example of synthesizing acrolein through action of supercritical water and acid with glycerin (partial view 2).

FIG. 11-3 shows an example of synthesizing acrolein through action of supercritical water and acid with glycerin (partial view 3).

FIG. 12-1 shows an example of synthesizing acrolein through action of supercritical water and acid with glycerin (partial view 1).

FIG. 12-2 shows an example of synthesizing acrolein through action of supercritical water and acid with glycerin (partial view 2).

FIG. 12-3 shows an example of synthesizing acrolein through action of supercritical water and acid with glycerin (partial view 3).

FIG. 13-1 shows an example of synthesizing acrolein through action of supercritical water and acid with glycerin (partial view 1).

FIG. 13-2 shows an example of synthesizing acrolein through action of supercritical water and acid with glycerin (partial view 2).

FIG. 13-3 shows an example of synthesizing acrolein through action of supercritical water and acid with glycerin (partial view 3).

FIG. 14-1 shows an example of synthesizing acrolein through action of supercritical water and acid with glycerin (partial view 1).

FIG. 14-2 shows an example of synthesizing acrolein through action of supercritical water and acid with glycerin (partial view 2).

FIG. 14-3 shows an example of synthesizing acrolein through action of supercritical water and acid with glycerin (partial view 3).

FIG. 15-1 shows an example of synthesizing acrolein through action of supercritical water and acid with glycerin (partial view 1).

FIG. 15-2 shows an example of synthesizing acrolein through action of supercritical water and acid with glycerin (partial view 2).

FIG. 15-3 shows an example of synthesizing acrolein through action of supercritical water and acid with glycerin (partial view 3).

FIG. 16-1 shows an example of synthesizing acrolein through action of supercritical water and acid with glycerin (partial view 1).

FIG. 16-2 shows an example of synthesizing acrolein through action of supercritical water and acid with glycerin (partial view 2).

FIG. 16-3 shows an example of synthesizing acrolein through action of supercritical water and acid with glycerin (partial view 3).

FIG. 17-1 shows an example of synthesizing acrolein through action of supercritical water and acid with glycerin (partial view 1).

FIG. 17-2 shows an example of synthesizing acrolein through action of supercritical water and acid with glycerin (partial view 2).

FIG. 17-3 shows an example of synthesizing acrolein through action of supercritical water and acid with glycerin (partial view 3).

BEST MODE FOR CARRYING OUT THE INVENTION

Figure 1:
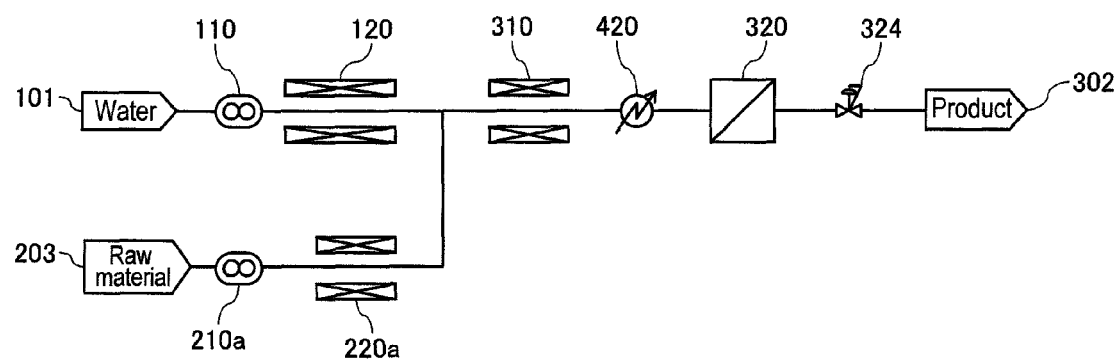
FIG. 1 shows conventional supercritical experimental equipment.

Embodiments of the present invention are configured basically as follows. That is, a cooler is divided, where in a first cooler (420) a reaction solution obtained through action of supercritical water and acid with an organic compound raw material is cooled to a temperature that stops a main reaction and can keep a high-viscosity component such as tar included in the reaction solution in a sufficiently lowered viscosity state. Thereby, the generation amount of a by-product can be reduced, and the viscosity and the adhesiveness of the high-viscosity component such as tar are not increased so as to keep a state free from agglomeration of solid components such as carbon particles.

In the state free from agglomeration of solid components such as carbon particles, the solid components have a particle diameter of several μm to several tens of μm, and have very small adhesiveness. Therefore, such solid components do not block pipes and the rise of differential pressure caused by adhesion and blockage with the solid matter can be suppressed even at a filter or a hydrocyclone that separates the solid matter for removal. Accordingly, the frequency of changing in plant operation systems and the maintenance frequency such as a filter backwash operation can be decreased remarkably, and so energy loss caused by stopping and resuming can be decreased, thus resulting in a decrease of operational cost.

Further, after the reaction solution at a high temperature such as at 400° C. is cooled, solid components are separated. Therefore, thermal degradation of a separator can be prevented. The reaction solution after the first cooling preferably has the viscosity of 0.1 Pa·s or less, and so the solution is required at a temperature realizing such a degree of low viscosity, specifically, at 100° C. or higher. On the other hand, in order to completely stop a synthesis reaction and a heat decomposition reaction, the solution preferably is at a temperature of 200° C. or lower. Accordingly, the solution after cooling by the first cooler preferably is at a temperature from 100 to 200° C.

In the first cooler (420), cooling water is directly mixed with the reaction solution, whereby a temperature change at the cooling temperature can be speeded up as compared with indirect heat exchange from the vicinity of a pipe such as using a jacket, and so the a heat decomposition reaction can be stopped speedily. As a result, acrolein generated can be prevented from changing to by-products such as tar and carbon particles, and so improvement of raw materials yield can be expected. Further, the generation amount of by-products is decreased, thus leading to suppression of blockage in a pipe or equipment as well as erosion generated due to the by-products generated and thus contributing to precise pressure control.

Next, after separating solid from the reaction solution for removal, the reaction solution is cooled in a second cooler (620) to a temperature that is the boiling point of water or lower, where tar components in the reaction solution does not adhere to equipment. Thereafter, the solution undergoes pressure reduction by a pressure-reducing valve (324). As for this pressure reduction operation, the pressure-reducing valve has a very small width and tends to be blocked. However, suppression of not only solid components but also tar components from adhering thereto enables an easy and stable opening/closing operation of the regulator. The adhesion of solid matter and tar to devices such as a tube, a filter and a valve is decreased in this way, whereby precision of pressure control by the pressure-reducing valve can be improved.

Further, since the cooling temperature set lower than the boiling point of water can suppress abrupt expansion of the volume of the reaction solution after pressure reduction, the reactor can have improved safety. The reaction solution after cooling by the second cooler preferably has the viscosity of 10 Pa·s or less, and so the solution is required at a temperature realizing such a degree of low viscosity, specifically at 53° C. or higher, preferably at 80° C. or higher. On the other hand, from the viewpoint of suppressing vaporization and abrupt expansion of the reaction solution after pressure reduction, the reaction solution preferably is at a temperature of 100 ° C. or lower. Accordingly, the reaction solution after cooling by the second cooler is at a temperature from 53 to 100° C., preferably at a temperature of 80 to 100° C. with consideration given to a temperature of the boiling point of acrolein or higher at minimum.

Figure 2:
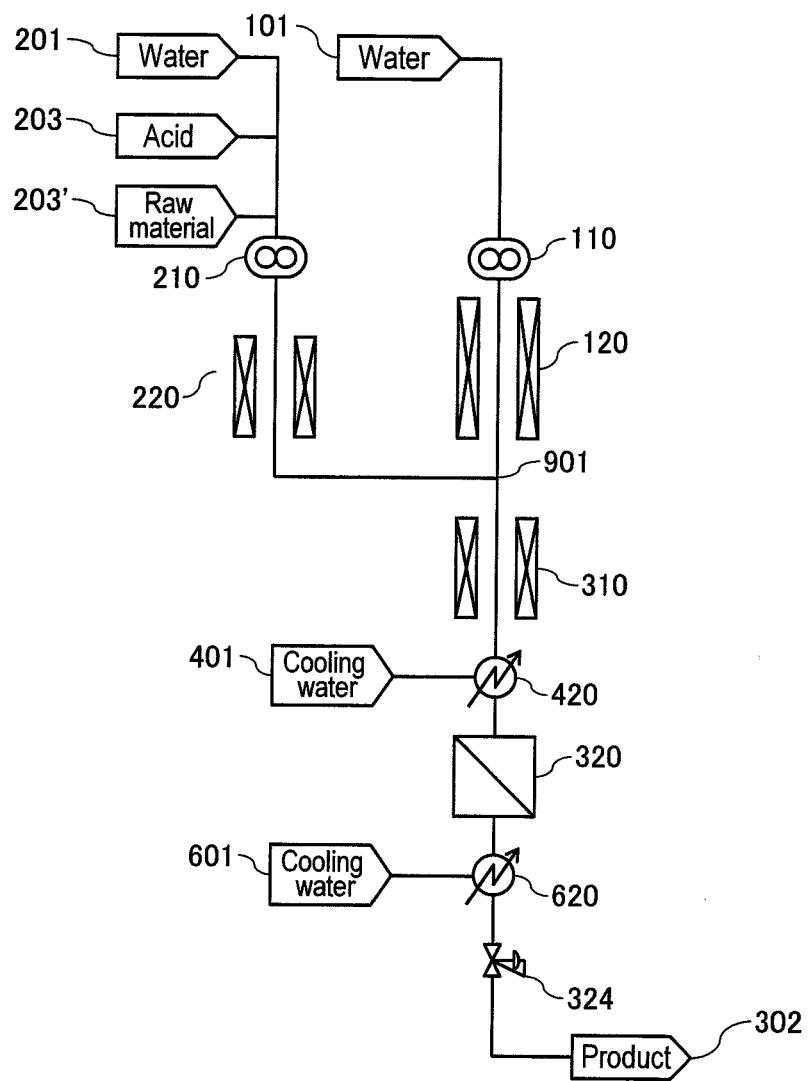
FIG. 2 shows a first embodiment of the present invention (two-stage cooling).

FIG. 2 shows a basic configuration of the aforementioned embodiment of the present invention. In FIG. 2, water is supplied to high-pressure pumps (110) and (210) from water headers (101) and (201), and the water is allowed to flow at a predetermined of flow rate similar to that at a synthesis reaction. After obtaining a stable flow rate, the pressure-reducing valve (324) is regulated until a pressure gauge (not illustrated) provided at a tube shows 35 MPa as a reaction pressure. After obtaining a stable pressure, preheaters (120) and (220) are heated depending on the flow rates of the high-pressure pumps (110) and (210) until a thermometer (not illustrated) provided upstream of the first cooler (420) shows 400° C. as a reaction temperature. At the same time, the temperature of a heater (310) is increased to 400° C. so as to hold the reaction temperature.

Cooling water is supplied from cooling water headers (401) and (601) to the cooler (420) and the cooler (620), respectively, which are provided upstream and downstream of a filter or a hydrocyclone (320), and the cooling water is mixed with the reaction solution to lower the temperature of the reaction solution. Flow rates of the cooling water supplied from the cooling water headers (401) and (601) are controlled by a supplying pump for cooling water (not illustrated) so that the reaction solution after mixture has temperatures at 100 to 200° C. and 53 to 100° C. (preferably 80 to 100° C.), respectively.

After obtaining the stable temperature at 400° C. and the stable pressure at 35 MPa on the upstream side of the first cooler (420) of a direct-mixture type, a valve (not illustrated) of the water header (201) is closed, and valves (not illustrated) of acid header (203) and a raw-material header (203') are opened so as to supply sulfuric acid and glycerin, respectively. Then, the reaction starts for acrolein synthesis, and acrolein is taken out from a product capture line (302).

In another embodiment of the present invention, a third cooler is disposed downstream of the pressure-reducing valve (324) to cool the reaction solution after pressure reduction to a temperature at a boiling point of a target reaction material or a temperature close thereto, whereby a target material can be easily vaporized from the reaction solution discharged from the third cooler. As a result, energy efficiency for reheating at a distillation step performed later can be improved. When the product is acrolein, the cooling temperature by the third cooler preferably is within a range around temperatures of 53° C. or higher as the boiling point of acrolein.

Figure 3:
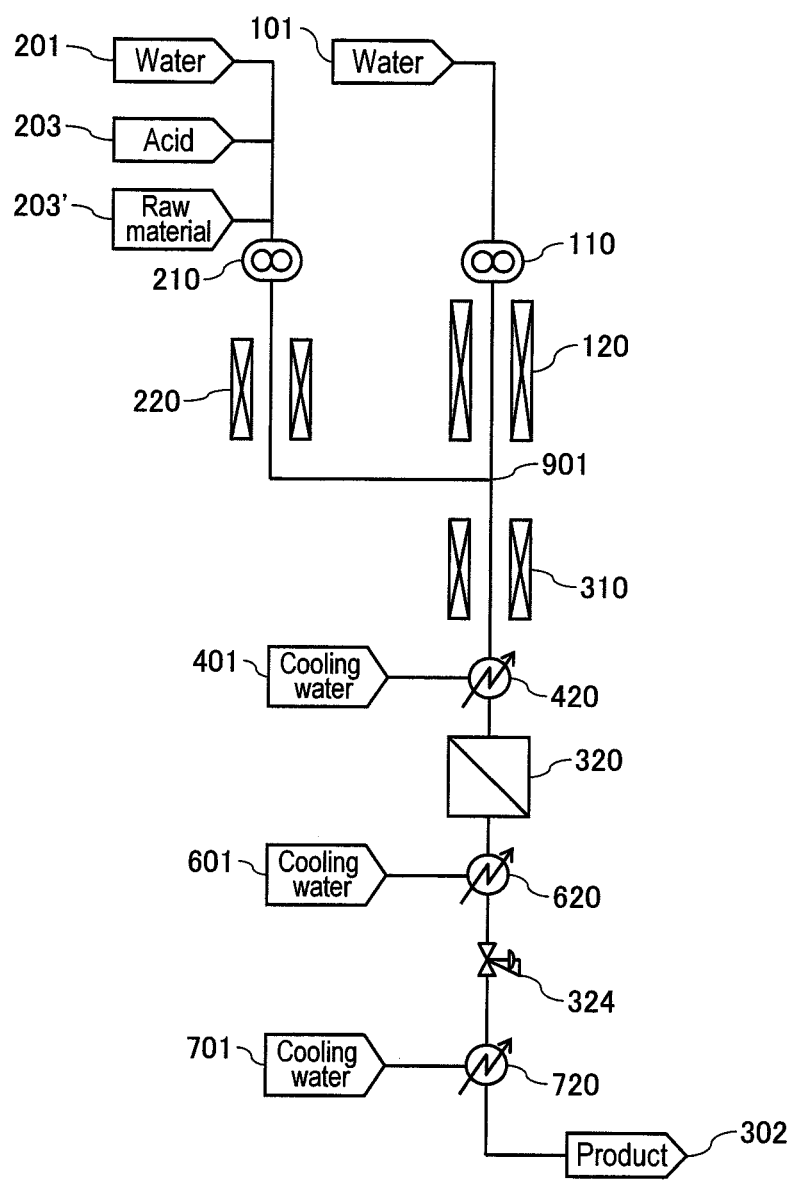
FIG. 3 shows a second embodiment of the present invention (three-stage cooling).

FIG. 3 shows a basic configuration of another embodiment provided with a third cooler (720) on the downstream side of the pressure-reducing valve (324) as well as a cooling water header (701) supplying water to the third cooler (720).

In any embodiment of FIG. 2 and FIG. 3, every procedure from the starting of the reaction to the separation for removal of solid matter as a by-product at the filter or the hydrocyclone (320) is preferably performed in a vertical pipe separated by valves. Thereby, the reaction solution including the by-product uniformly flows down by gravity with respect to the circumferential direction of the pipe, and therefore smooth contact of solid matter particles with the inner face of the pipe can be obtained. As a result, erosion at a bottom part of a pipe, a pressure-reducing valve or the like due to accumulation of solid matter can be reduced, which is often generated in the case of a horizontal system.

Further, a plurality of systems may be provided in parallel for the process from the reactor to the pressure-reducing valve, whereby alternate operation by changing the systems is enabled, and maintenance such as emission of deposition by washing can be performed for a system during non-operation. Even during maintenance of one system, the other system of the plurality of systems allows continuous operation without stopping the plant as a whole, and allows enough time for the maintenance operation.

Figure 4:
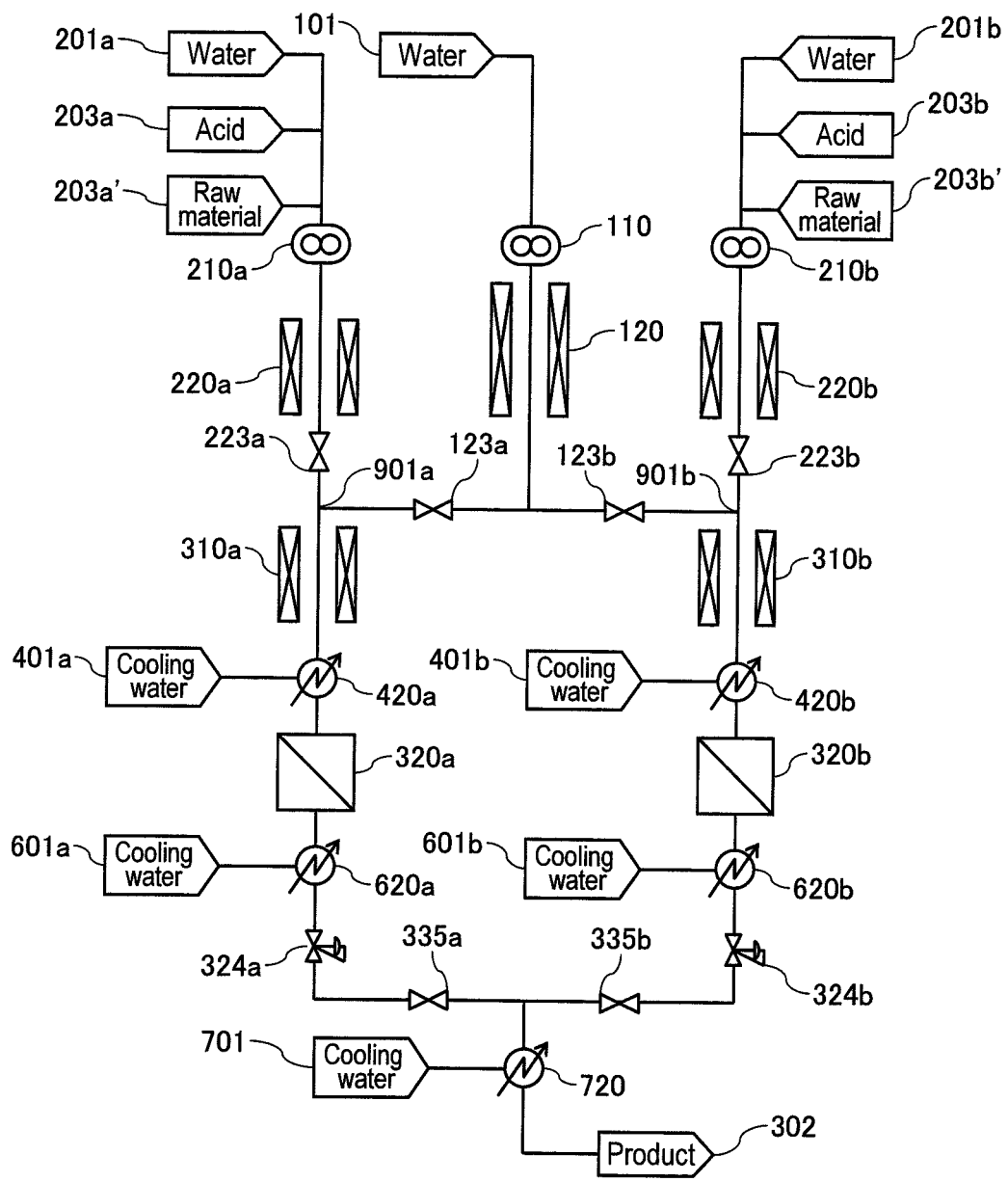
FIG. 4 shows a third embodiment of the present invention (two-system reaction).

FIG. 4 illustrates a basic configuration of Embodiment 3 provided with parallel two systems from reactors to pressure-reducing valves (a-system and b-system lines). In this embodiment, the a-system is firstly activated to capture a product. During the operation of this a-system, when a differential pressure between the pressure measured by a pressure gauge (not illustrated) provided downstream of the filter or the hydrocyclone (320a) and the pressure measured by any one of pressure gauges (not illustrated) provided downstream of high-pressure pumps (110) and (210a) exceeds a predetermined value, that is, when a sign for the blockage at the filter or the hydrocyclone (320a) due to a by-product of the reaction mainly including carbon particles is shown, the b-system is activated. After the activation and during the operation of the b-system, the a-system undergoes maintenance. After decreasing the temperatures of a preheater (220a) and a heater (310a) to predetermined temperatures, the cooling of the a-system is continued, and thereafter the a-system line is washed. After finishing the washing of the line, the pump (210a) is stopped, and the filter (320a) is back-washed with washing fluid. Thereafter, the filter (320a) is back-washed with water. Next, the a-system line is washed with water.

During the operation of the b-system, when a differential pressure between the pressure measured by a pressure gauge (not illustrated) provided downstream of the filter or the hydrocyclone (320b) and the pressure measured by any one of pressure gauges (not illustrated) provided downstream of high-pressure pumps (110) and (210b) exceeds a predetermined value, that is, when a sign for the blockage at the filter or the hydrocyclone (320b) due to a by-product of the reaction mainly including carbon particles is shown, the a-system is activated, and then the b-system undergoes maintenance. In this way, the a-system and the b-system are changed alternately, thus enabling continuous production in the plant.

The preheater (120) making up the first-half stage of the reactor has a device size larger than that of the heater (310) of the reaction pipe because the solution stays longer in the former. Further, organic matter such as a raw material is not present at the preheater (120) portion, and so a by-product is not generated there. This means that the preheater portion has a large energy usage ratio in the overall process, but has much less trouble with a by-product as compared with the downstream side process. Then, when considering the method of a plurality of systems, the preheater (120) is shared among the systems, and the reaction pipe or later is branched into the plurality of systems, whereby the preheater (120) portion can be continuously operated even when a system in the downstream side process undergoes maintenance. Therefore, energy loss due to stopping and resuming can be minimized, and both of the facility cost and the operational cost can be reduced.

From these viewpoints, in Embodiment 3 illustrated in FIG. 4, a line including a water header (101), the high-pressure pump (110) and the preheater (120) is shared between the a-system and the b-system lines.

Acrolein can be used to synthesize acrylic materials, or can undergo a hydration/hydrogenation reaction to synthesize 1,3-propanediol. Then, this 1,3-propanediol is polymerized with terephthalic acid, whereby PTT as one of high-quality polyester used for fiber can be produced. Therefore, when the aforementioned embodiments are applied to the production of acrolein, the present invention enables a PTT raw material based on biomass, and so can contribute to reduction in consumption of fossil fuels with limited amount of deposit.

The following describes specific examples of the present invention in more detail. Note that the present invention is not limited to the following examples.

EXAMPLE 1

FIGS. 5 to 17 illustrate examples for a synthesis method of the present invention. Referring now to these drawings, the following describes an operating method for synthesizing acrolein through the action of supercritical water and acid with glycerin.

Figures 1, 5:
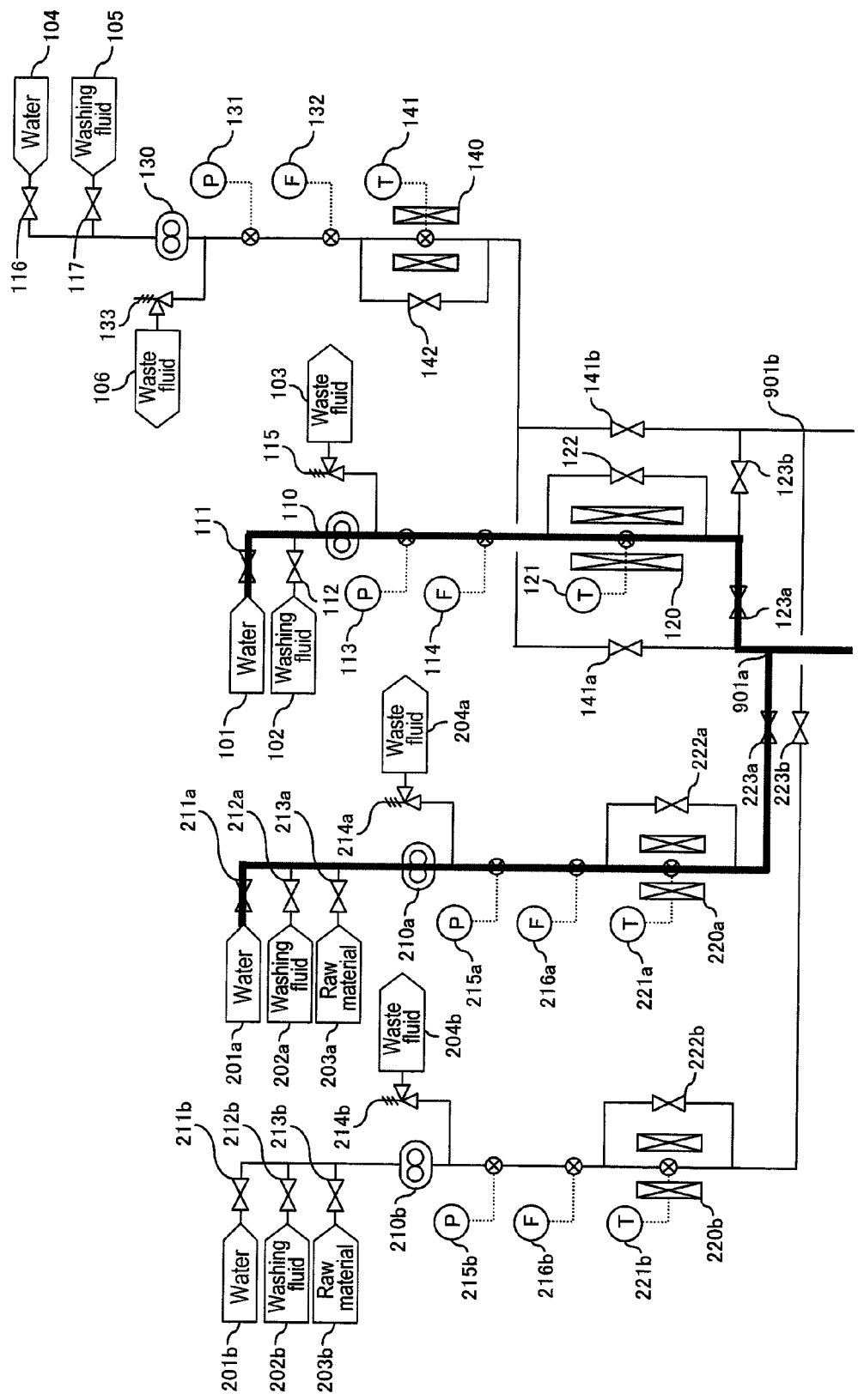
Figures 2, 5:
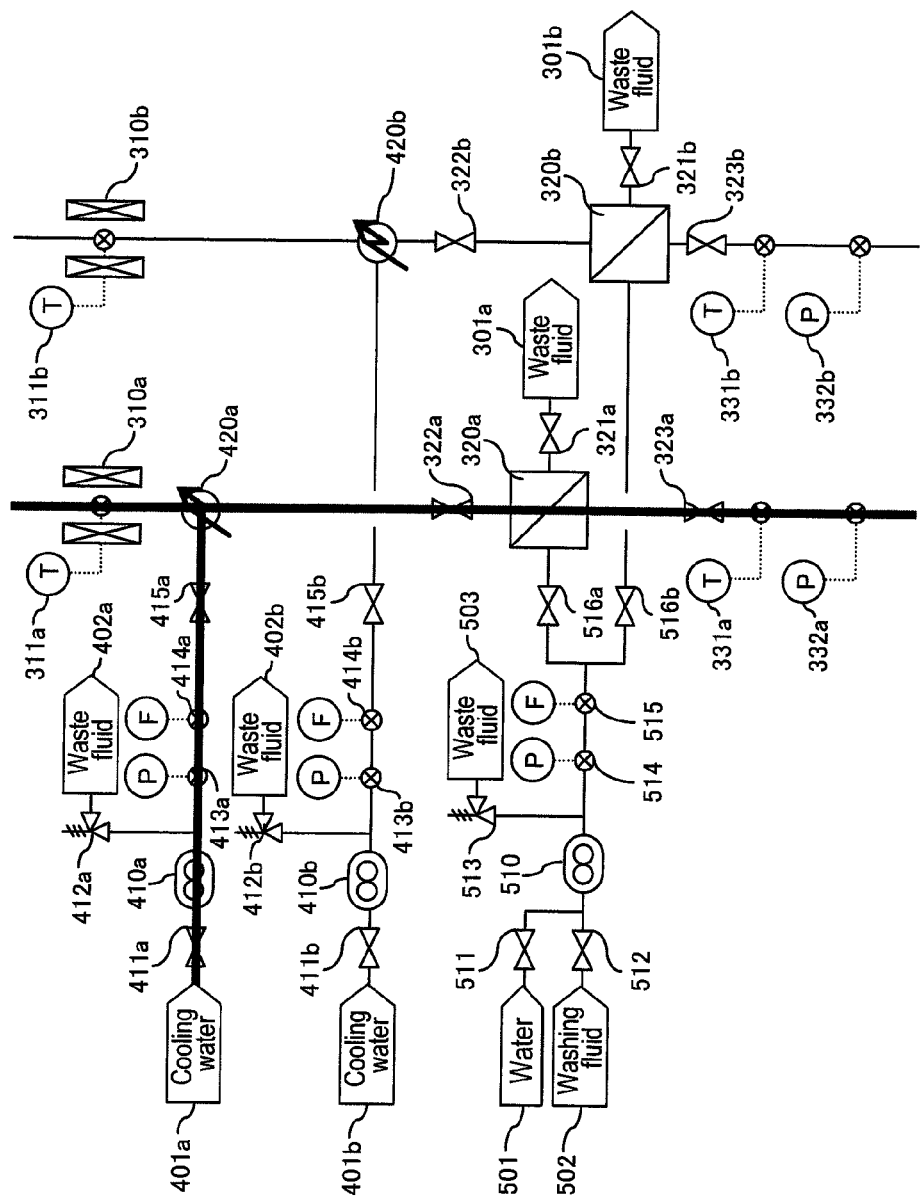
Figures 3, 5:
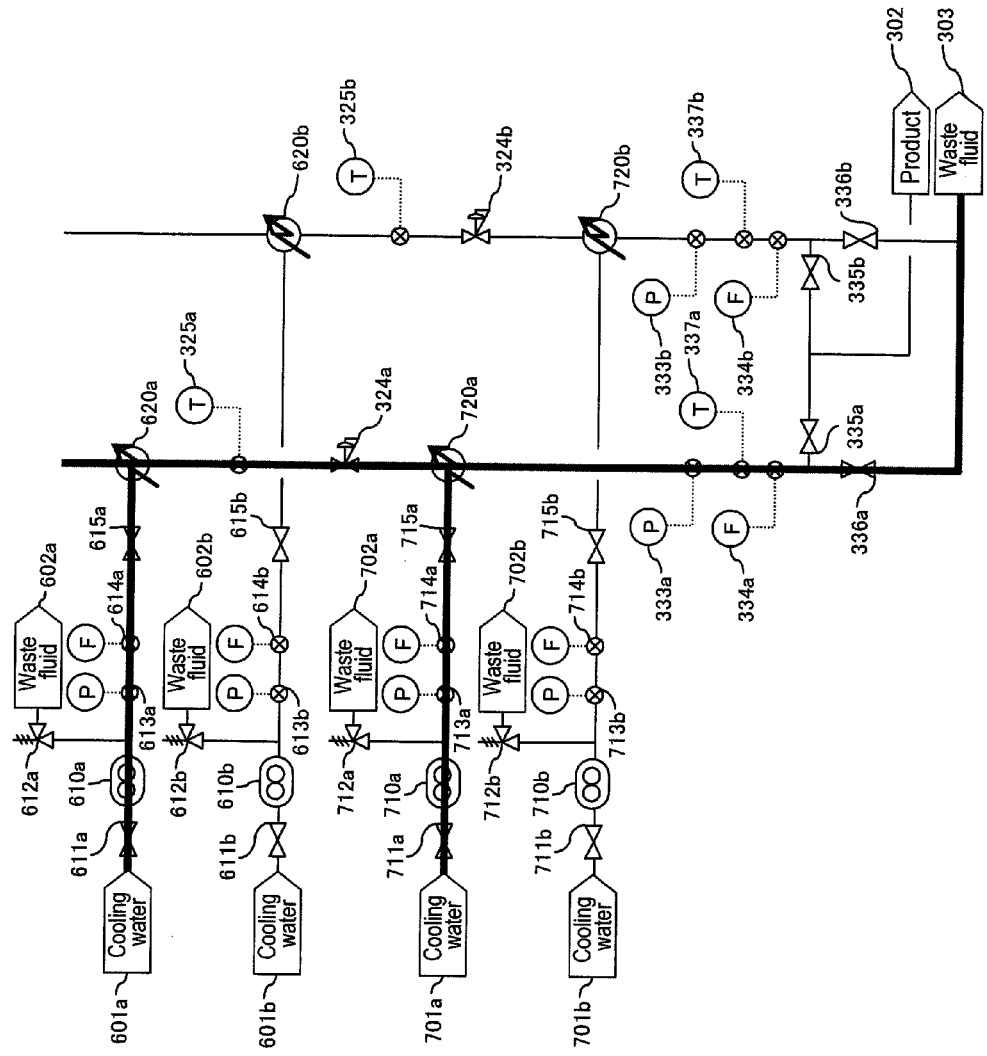

Reaction systems include two systems of a-system and b-system, and the a-system is firstly activated. As illustrated in FIG. 5, water is supplied from water headers (101), (201a), (401a), (601a) and (701a) to high-pressure pumps (110), (210a), (410a), (610a) and (710a), respectively, to let water flow at a predetermined flow rate equal to that during a synthesis reaction. After sending water of the pipe volume or more and obtaining a stable flow rate, a pressure-reducing valve (324a) is regulated to increase pressure until a pressure gauge (332a) indicates 35 MPa as reaction pressure. After obtaining stable pressure, preheaters (120), (220a) are heated to predetermined temperatures depending on the flow rate ratio of the high-pressure pumps (110), (210a) so that a thermometer (311a) indicates 400° C. as a reaction temperature. At the same time, in order to keep the reaction temperature, the temperature of a heater (310a) is increased to 400° C. Flow rates of the high-pressure pumps (410a), (610a) and (710a) are controlled so that thermometers (331a), (325a) and (337a) indicate 200° C., 80° C. and 53° C., respectively. Although a target temperature after first-stage cooling is set at 200° C., this may be a temperature less than 200° C. to 100° C.

Figures 1, 6:
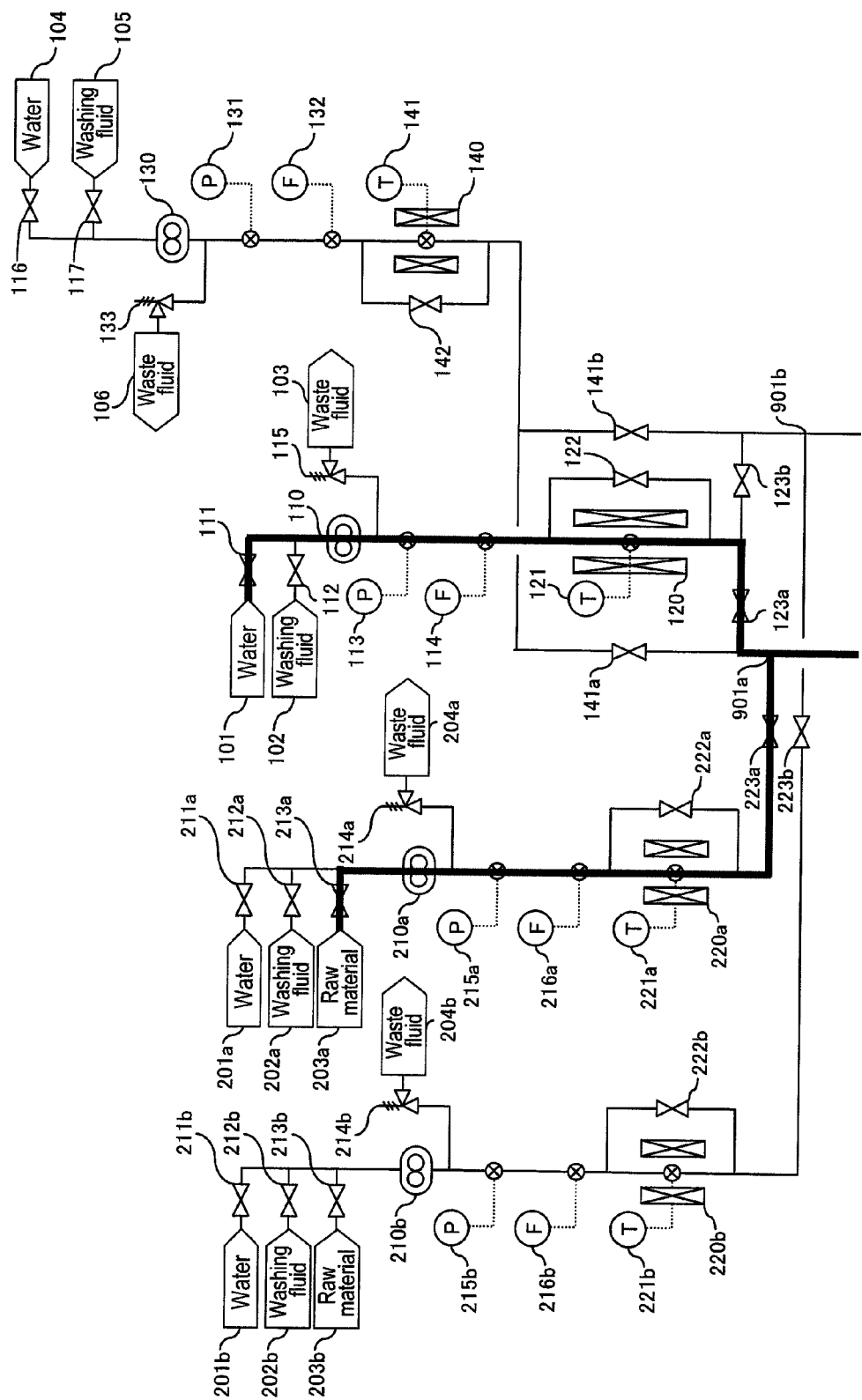
Figures 2, 6:
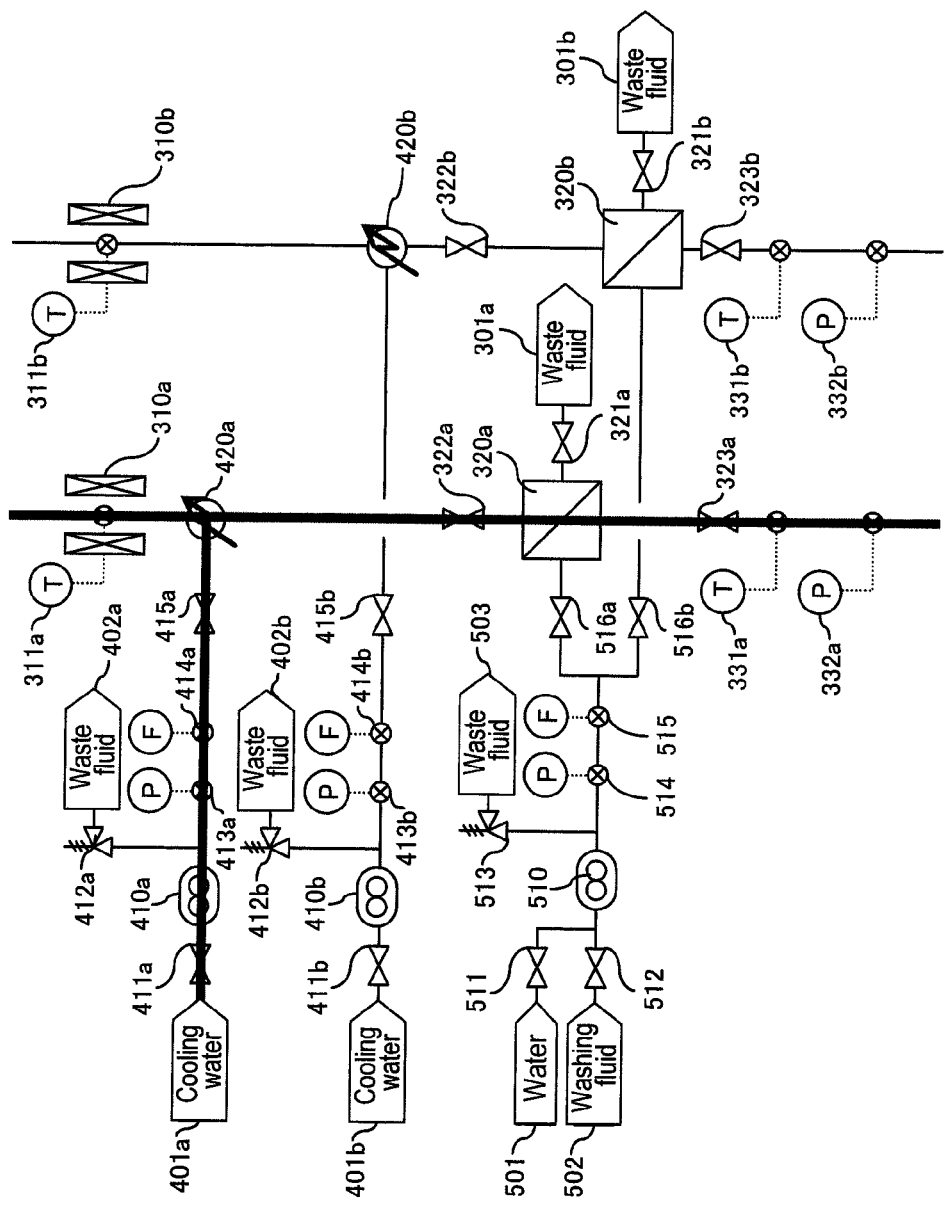
Figures 3, 6:
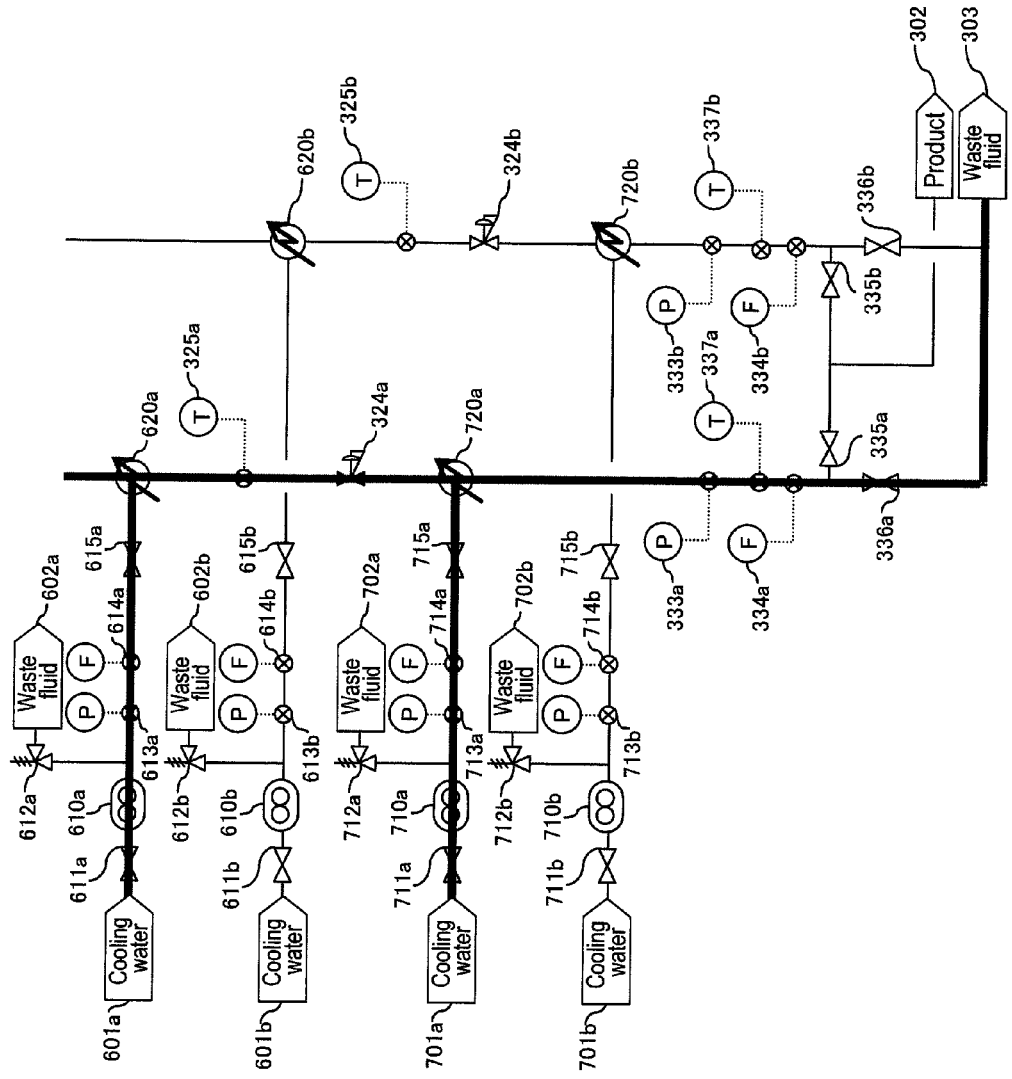
Figures 1, 7:
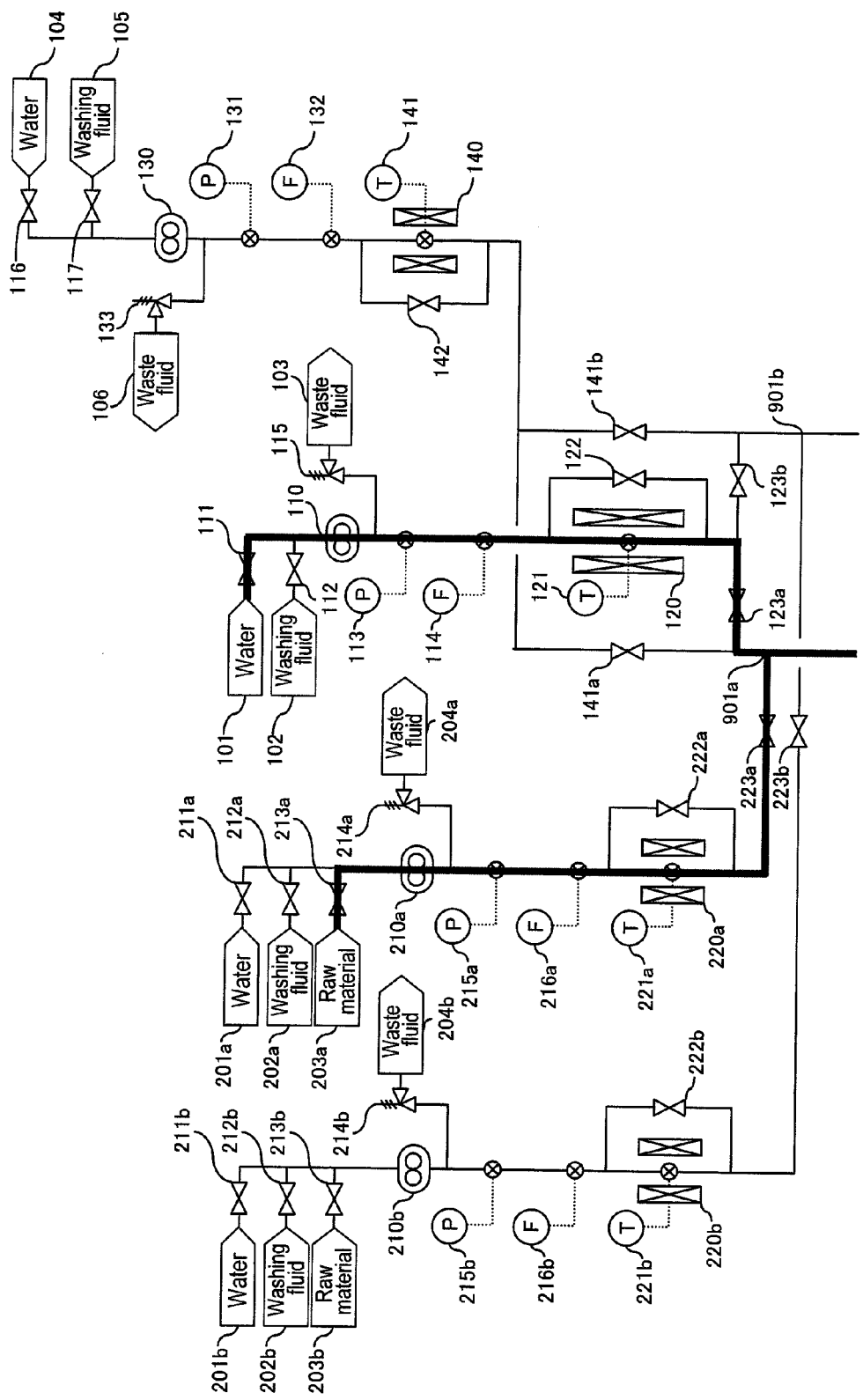
Figures 2, 7:
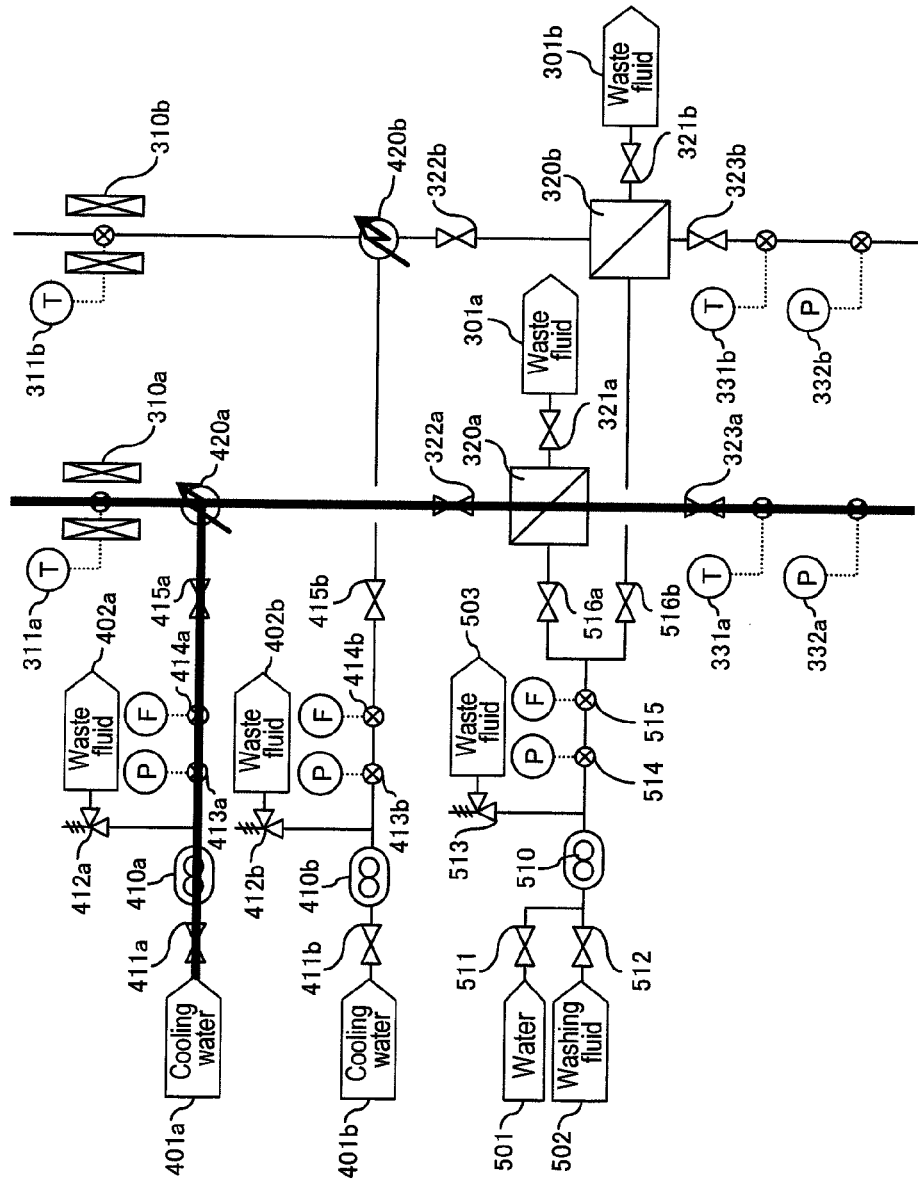
Figures 3, 7:
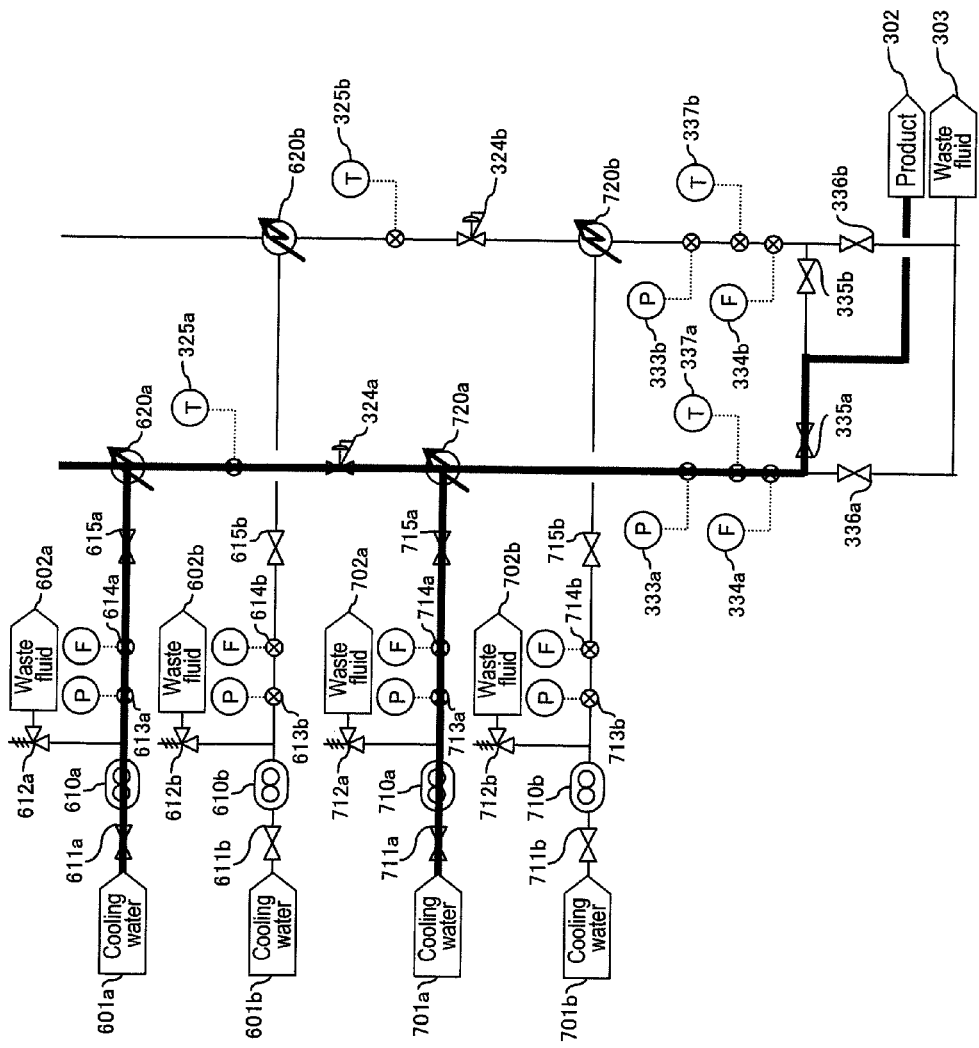

After the thermometer (311a) and the pressure gauge (332a) stably indicate 400° C. and 35 MPa, respectively, a raw material header valve (213a) is opened as illustrated in FIG. 6 and a water header valve (211a) is closed so as to let an aqueous solution of glycerin and sulfuric acid flow and let the action start. Next, after the amount of solution sent reaches three times the pipe volume, as illustrated in FIG. 7, a valve (335a) is opened and a valve (336a) is closed simultaneously to start the capturing of a reaction solution.

Figures 1, 8:
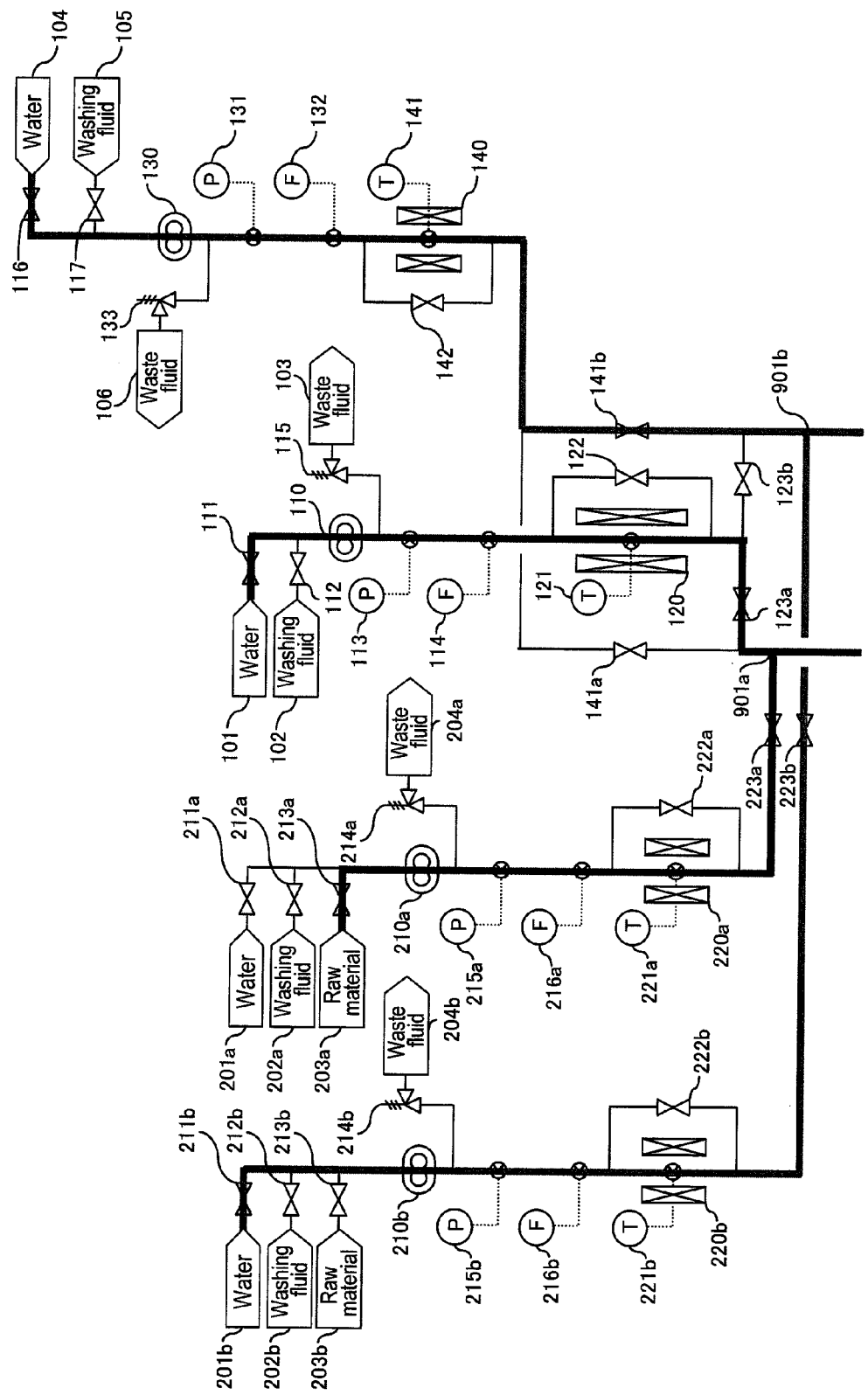
Figures 2, 8:
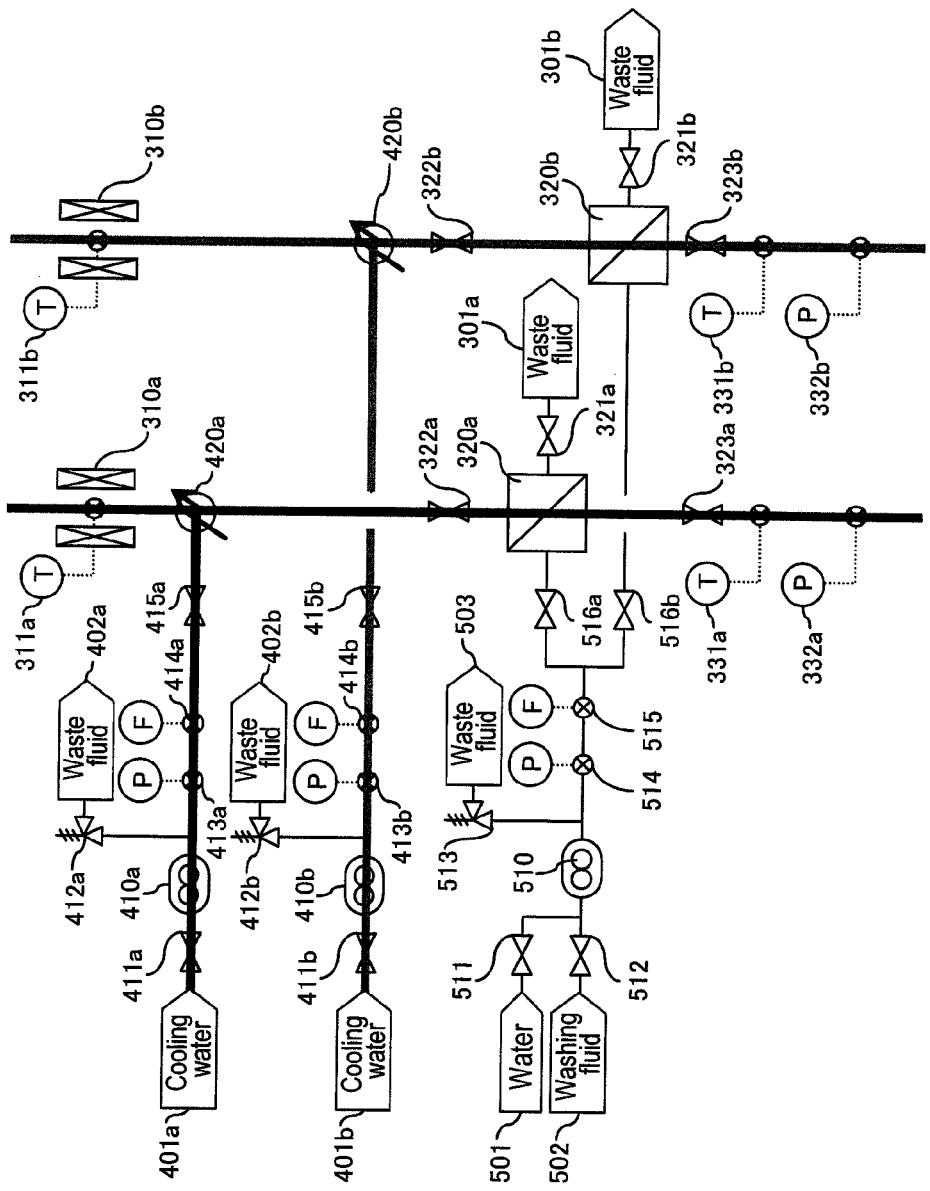
Figures 3, 8:
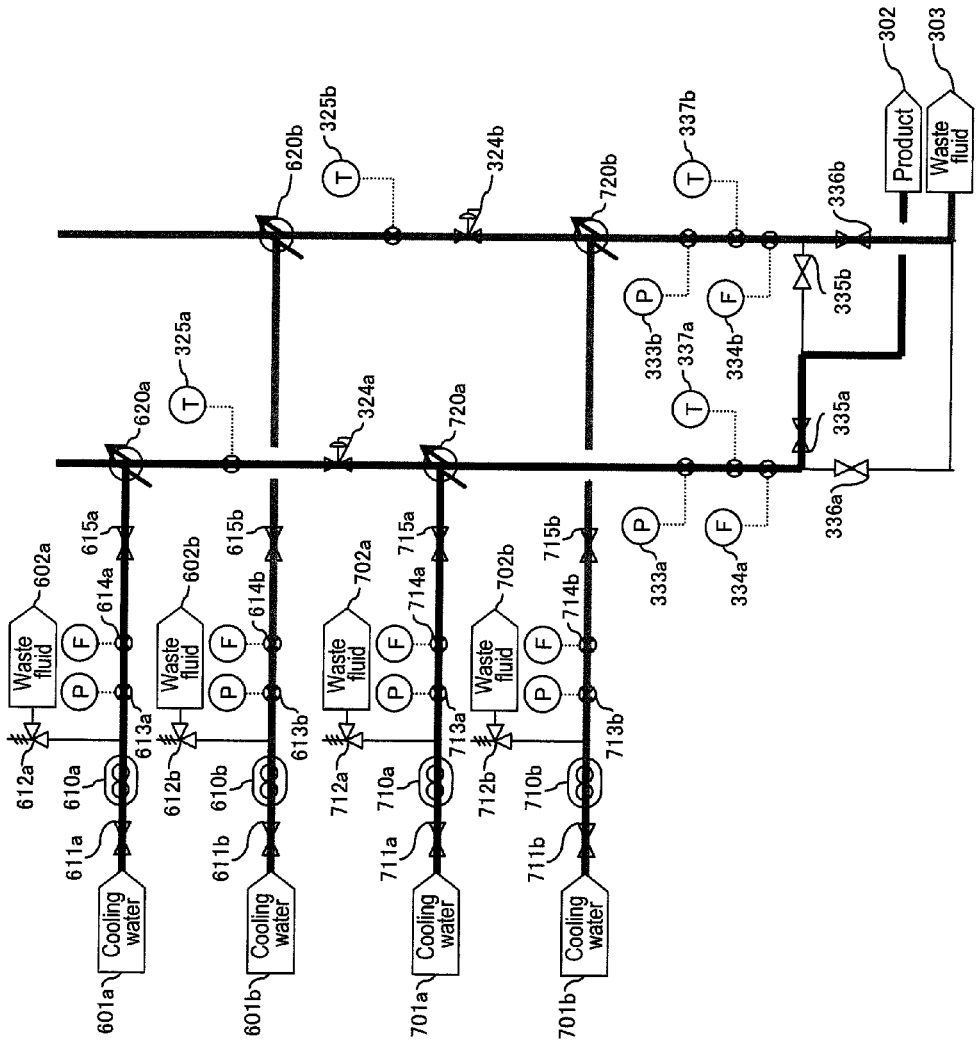

When a differential pressure between a pressure gauge (215a) or (113) and the pressure gauge (332a) exceeds a predetermined value, that is, when a sign for the blockage at a filter or a hydrocyclone (320a) due to a by-product of the reaction mainly including carbon particles is shown, the b-system is activated as illustrated in FIG. 8. Similarly to the activation of the a-system, water is supplied from water headers (104), (201b), (410b), (601b) and (701b) to high-pressure pumps (130), (210b), (410b), (610b) and (710b) to let water flow at a flow rate equal to that during a synthesis reaction. After sending water of the pipe volume or more and obtaining a stable flow rate, a pressure-reducing valve (324b) is regulated to increase pressure until a pressure gauge (332b) indicates 35 MPa as reaction pressure.

Next, a pipe of the b-system is preheated. After obtaining a stable indication value of the pressure gauge (332b), the pipe is heated by a heater (140) until a thermometer (141) indicates 200° C. Further, the output from a heater (220b) is regulated so that a thermometer (221b) indicates the same temperature as that for an actual synthesis reaction. At the same time, the output from a heater (310b) is regulated so that a thermometer (311b) indicates about 200° C.

Figures 1, 9:
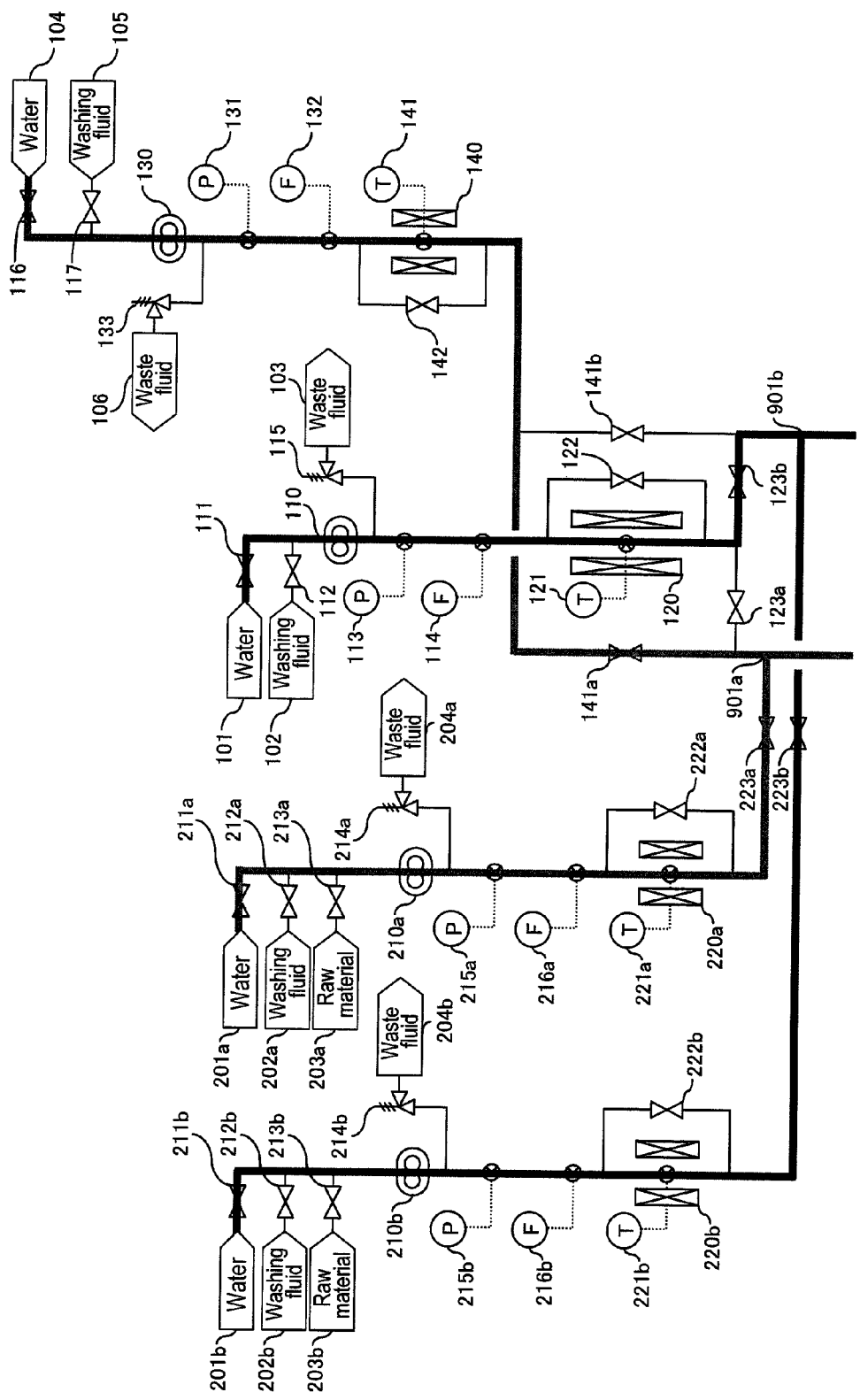
Figures 2, 9:
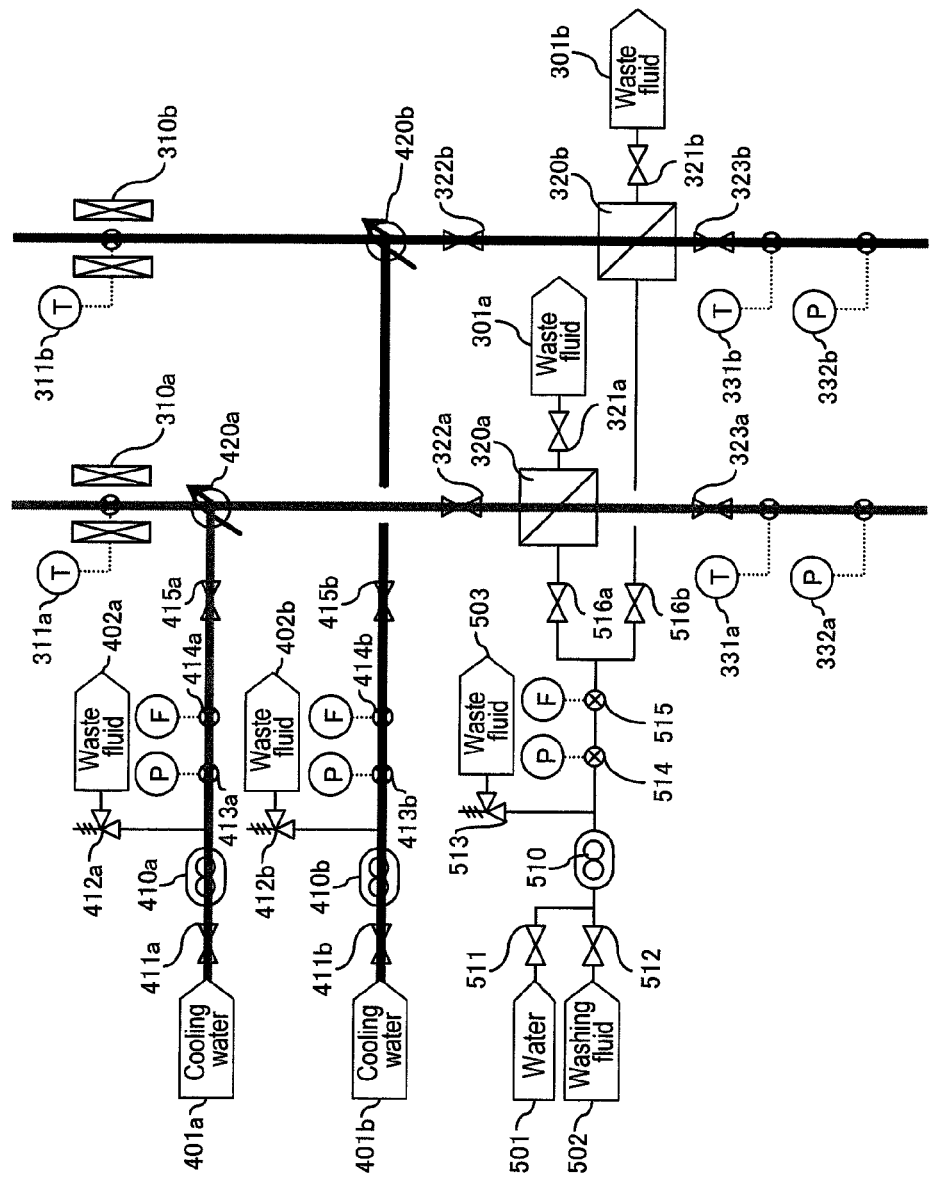
Figures 3, 9:
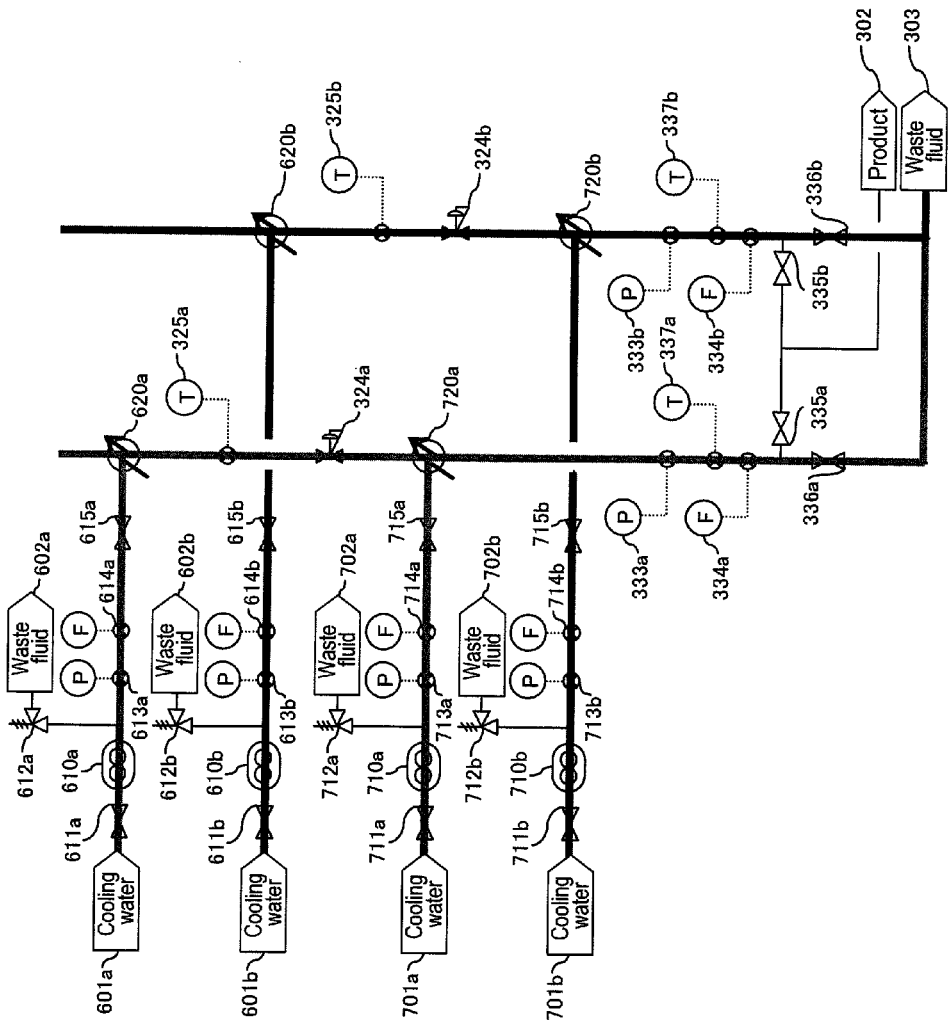

After obtaining a stable pipe temperature in the b-system, as illustrated in FIG. 9, the b-system is post-heated and the a-system is cooled by water. After a valve (123b) is opened and a valve (123a) is closed simultaneously, the outputs of preheaters (120), (220b) are regulated depending on the flow rate ratio of the high-pressure pumps (210b), (110) so that the thermometer (311b) indicates 400° C. as a reaction temperature. At the same time, in order to keep the temperature of the reaction pipe at 400° C. as the reaction temperature, the temperature of the heater (310b) is increased to 400° C. so as to post-heat the b-system. After a valve (141a) is opened and a valve (141b) is closed simultaneously, the preheaters (220a), (140) and the heater (310a) are stopped to cool the a-system. Flow rates of the high-pressure pumps (410b), (610b) and (710b) are controlled so that thermometers (331b), (325b) and (337b) indicate 200° C., 80° C. and 53° C., respectively.

Figures 1, 10:
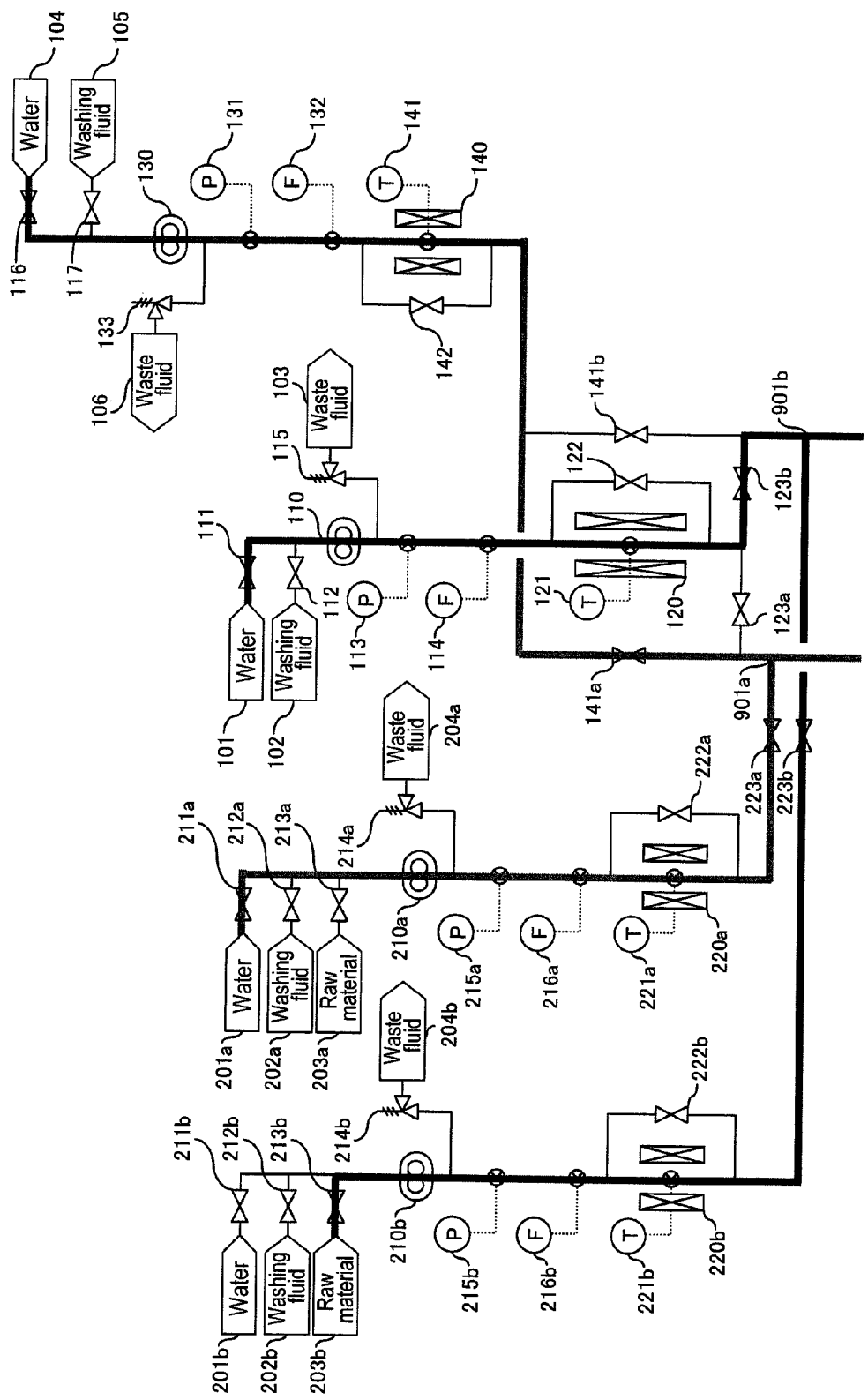
Figures 2, 10:
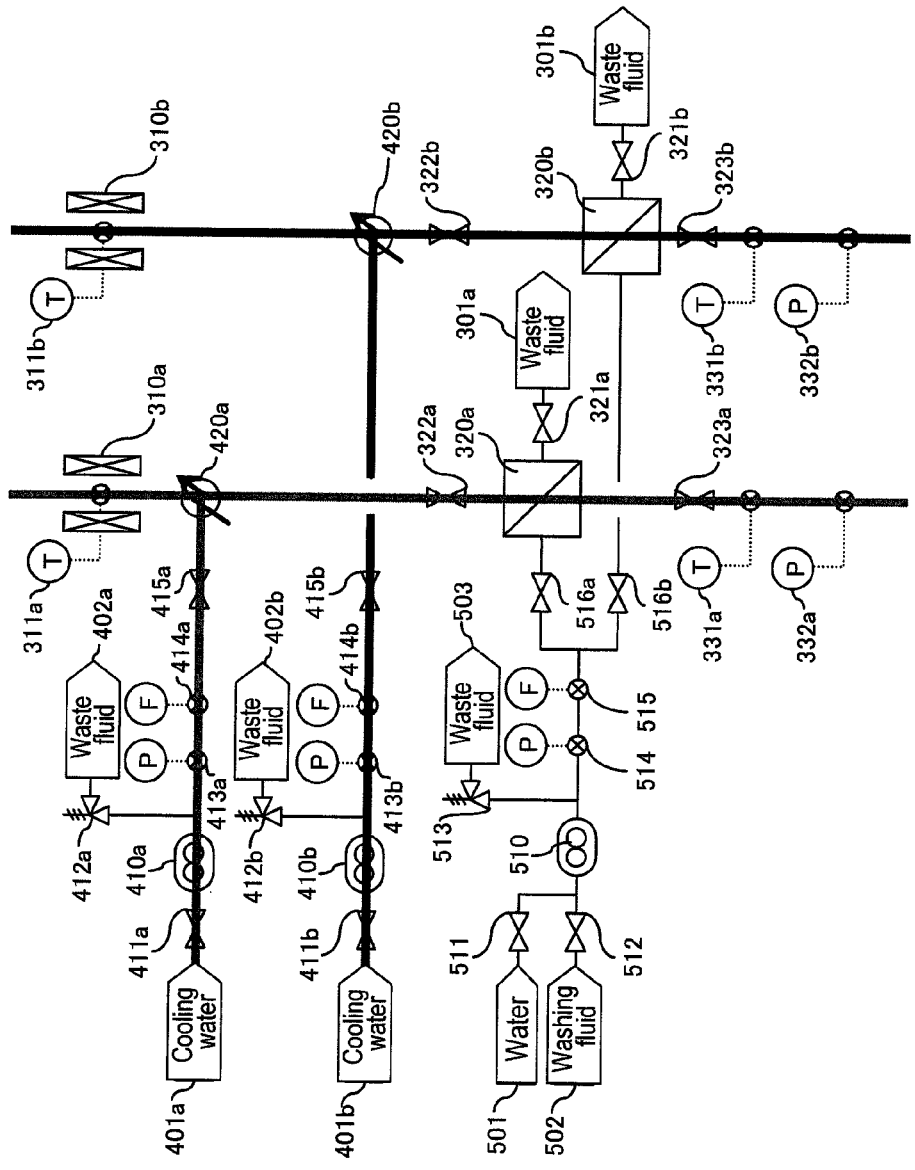
Figures 3, 10:
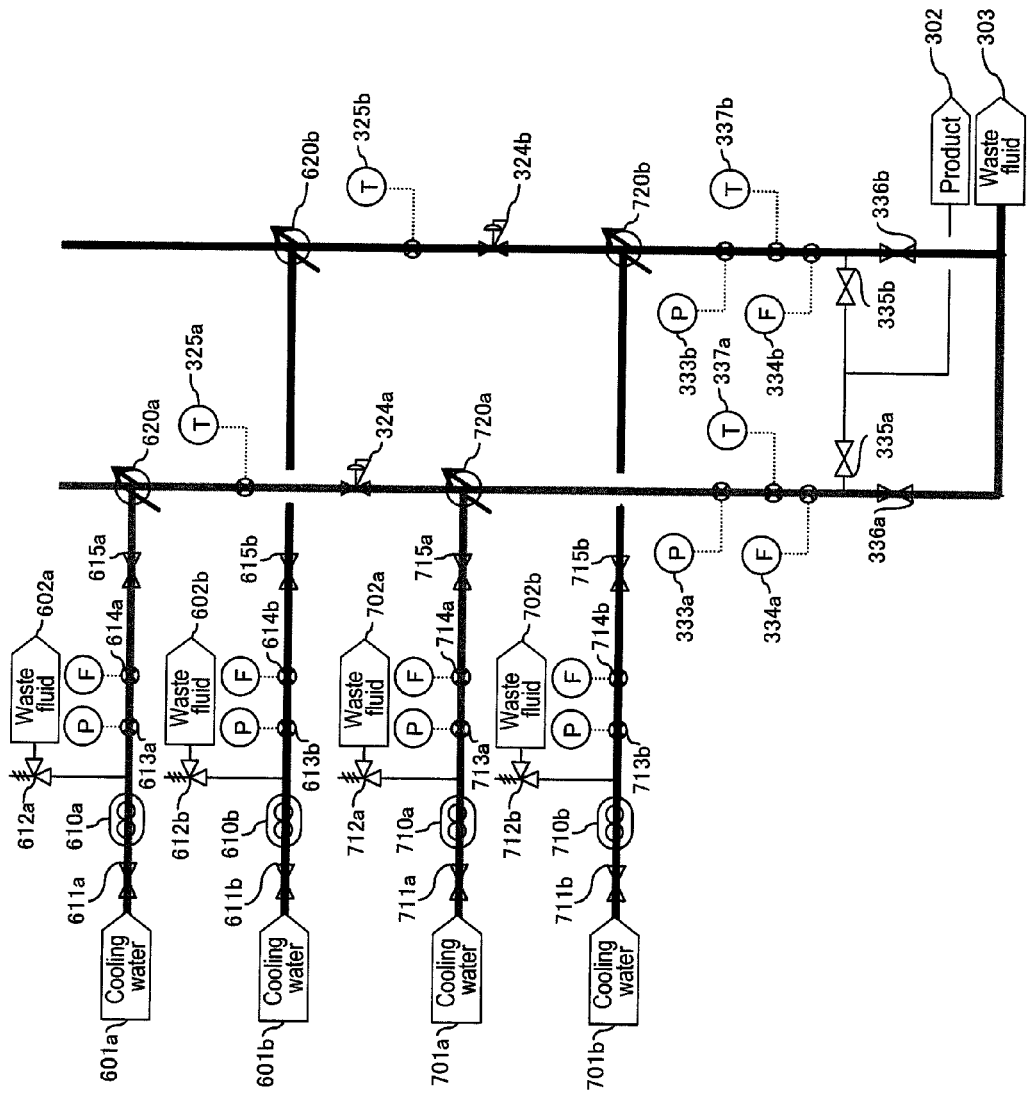
Figures 1, 11:
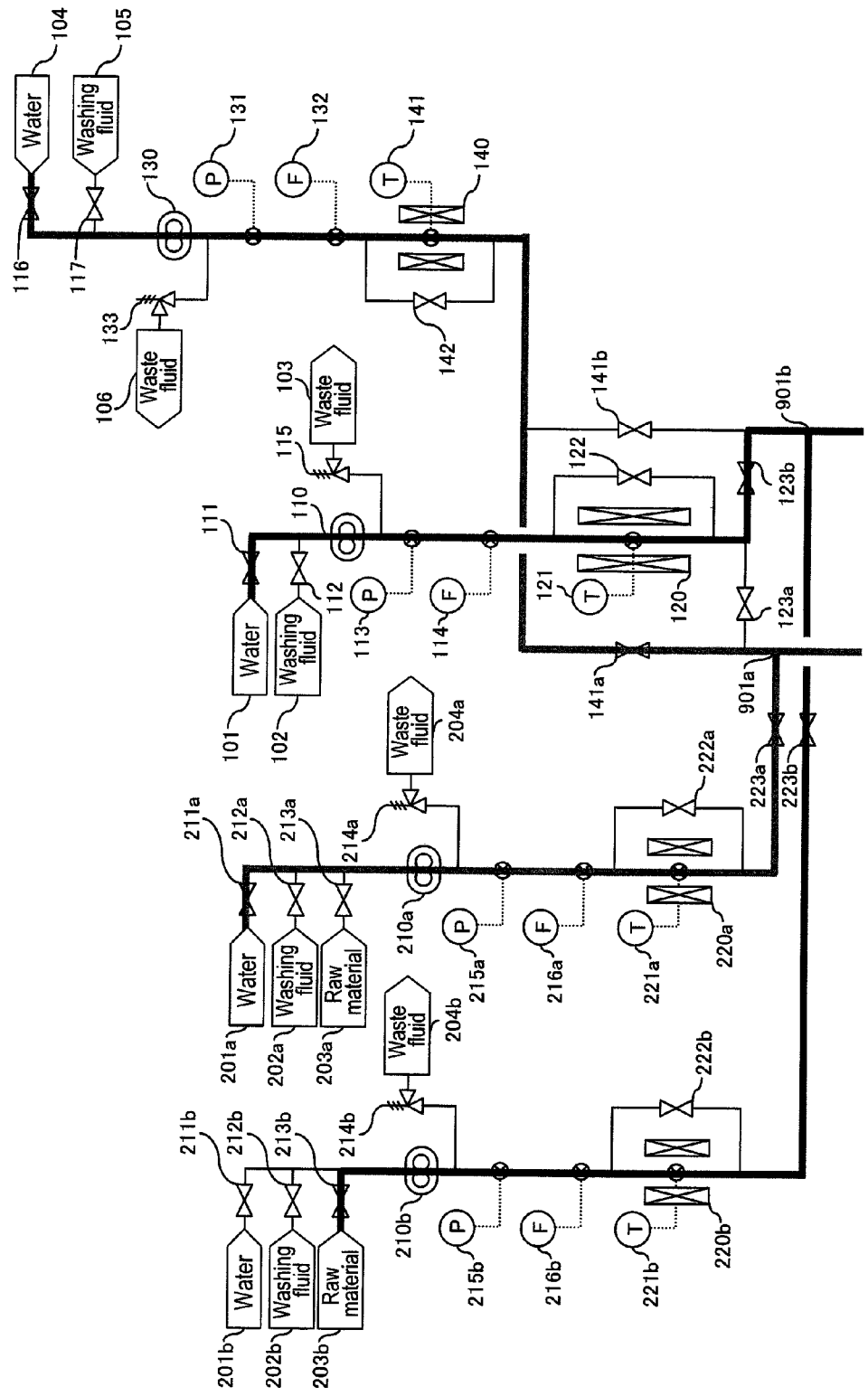
Figures 2, 11:
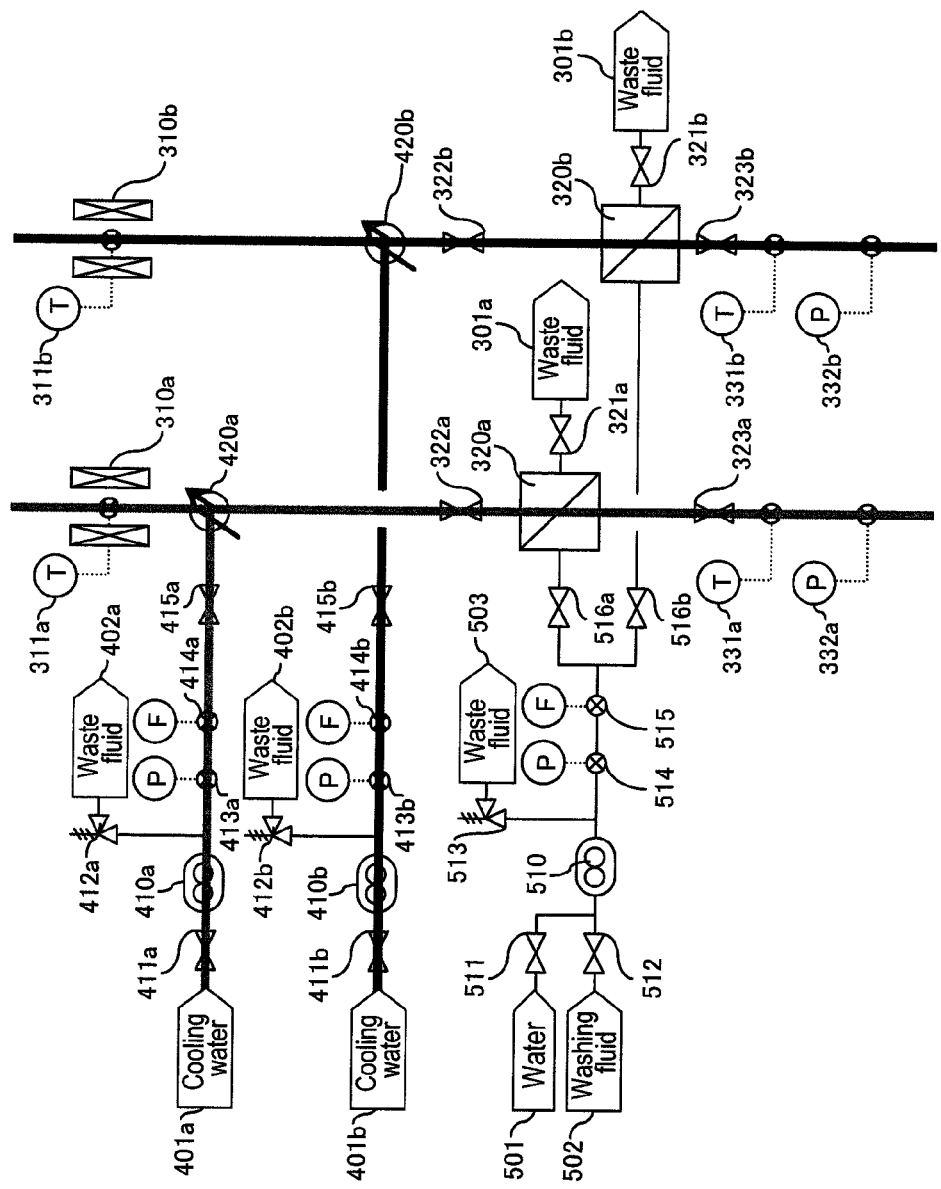
Figures 3, 11:
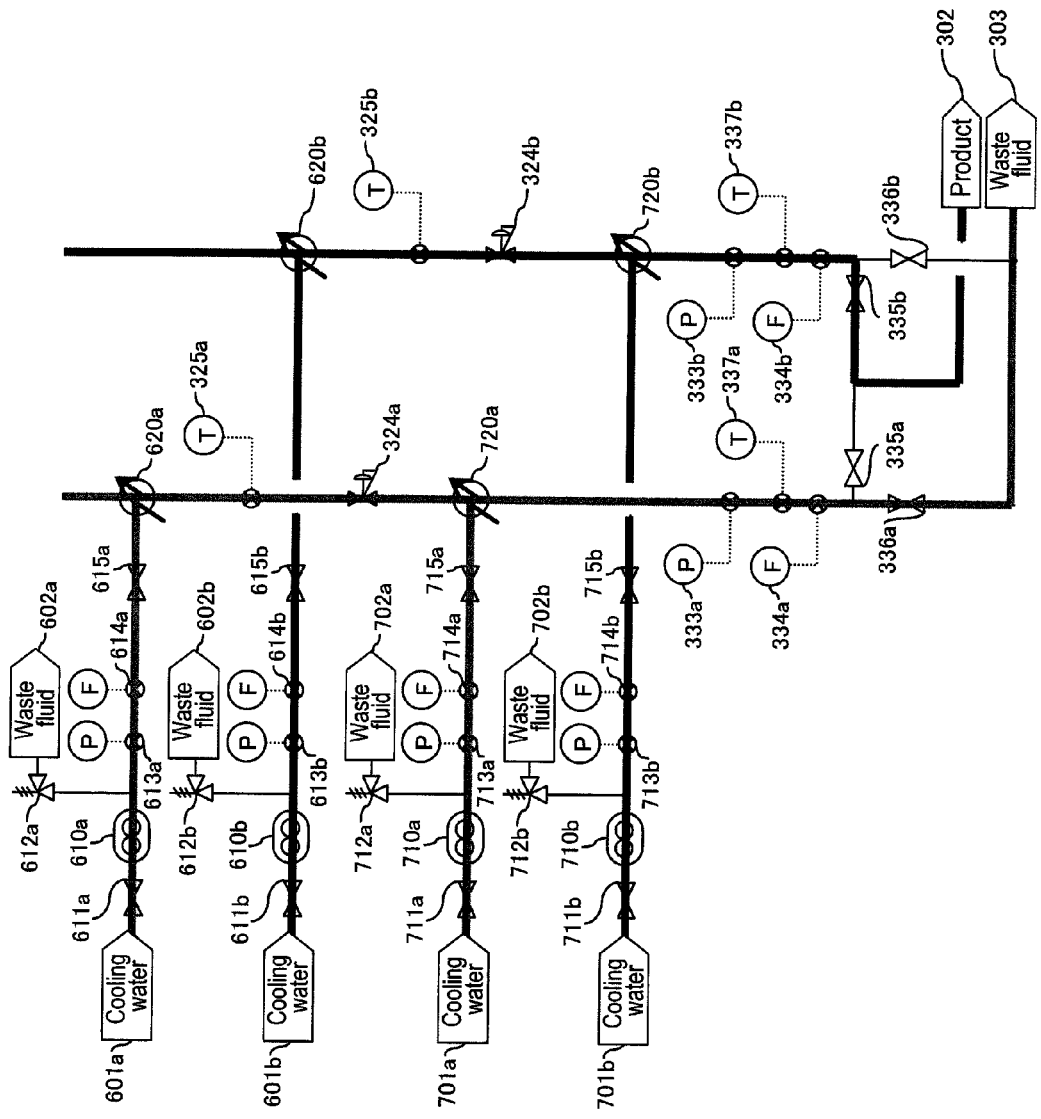

After the thermometer (311b) and the pressure gauge (332b) stably indicate 400° C. and 35 MPa, respectively, a raw material header valve (213b) is opened as illustrated in FIG. 10 and a water header valve (211b) is closed so as to let an aqueous solution of glycerin and sulfuric acid flow and let the action start in the b-system. Next, after the amount of solution sent reaches three times the pipe volume, as illustrated in FIG. 11, a valve (335b) is opened and a valve (336b) is closed simultaneously to start the capturing of a reaction solution.

Figures 1, 12:
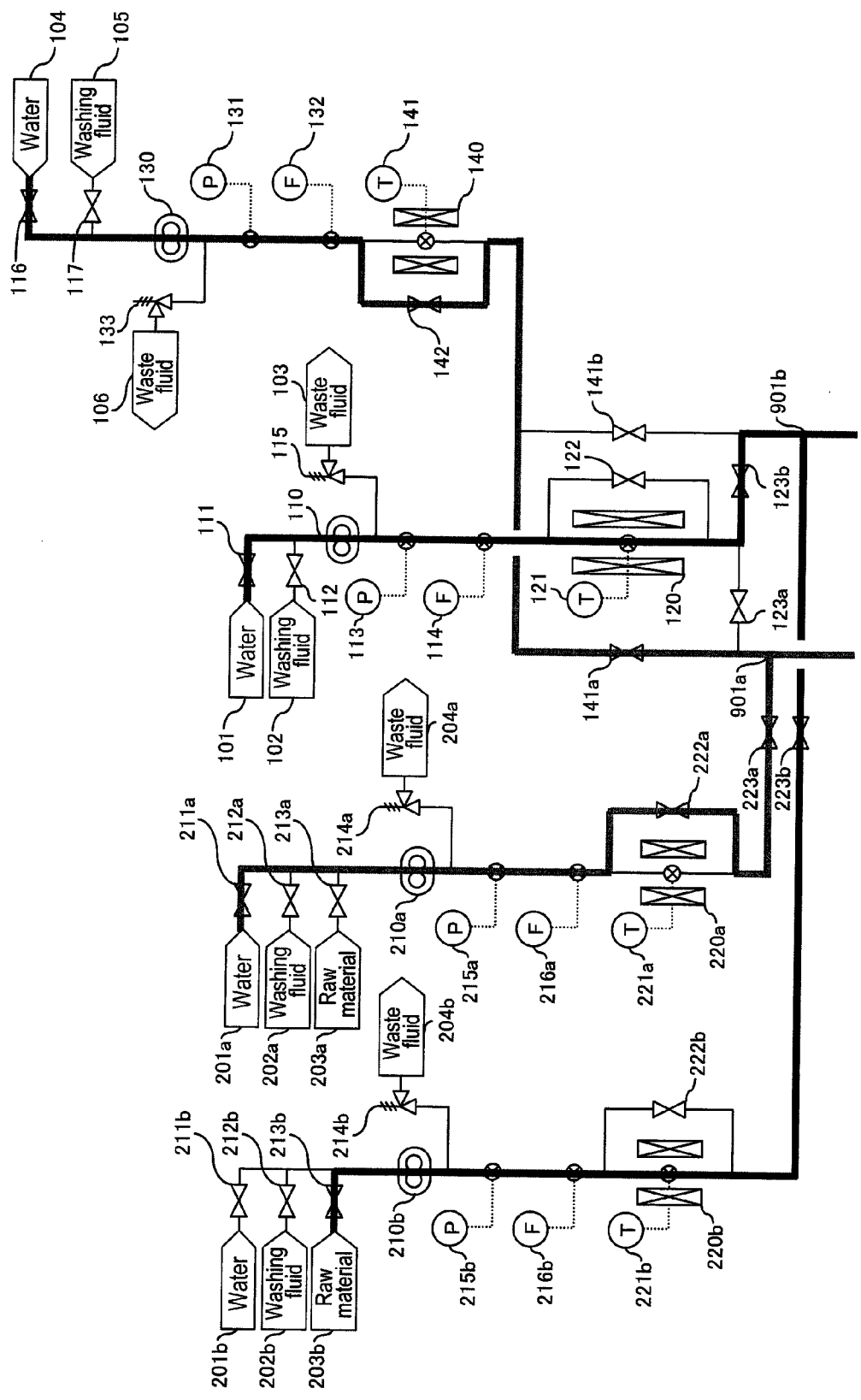
Figures 2, 12:
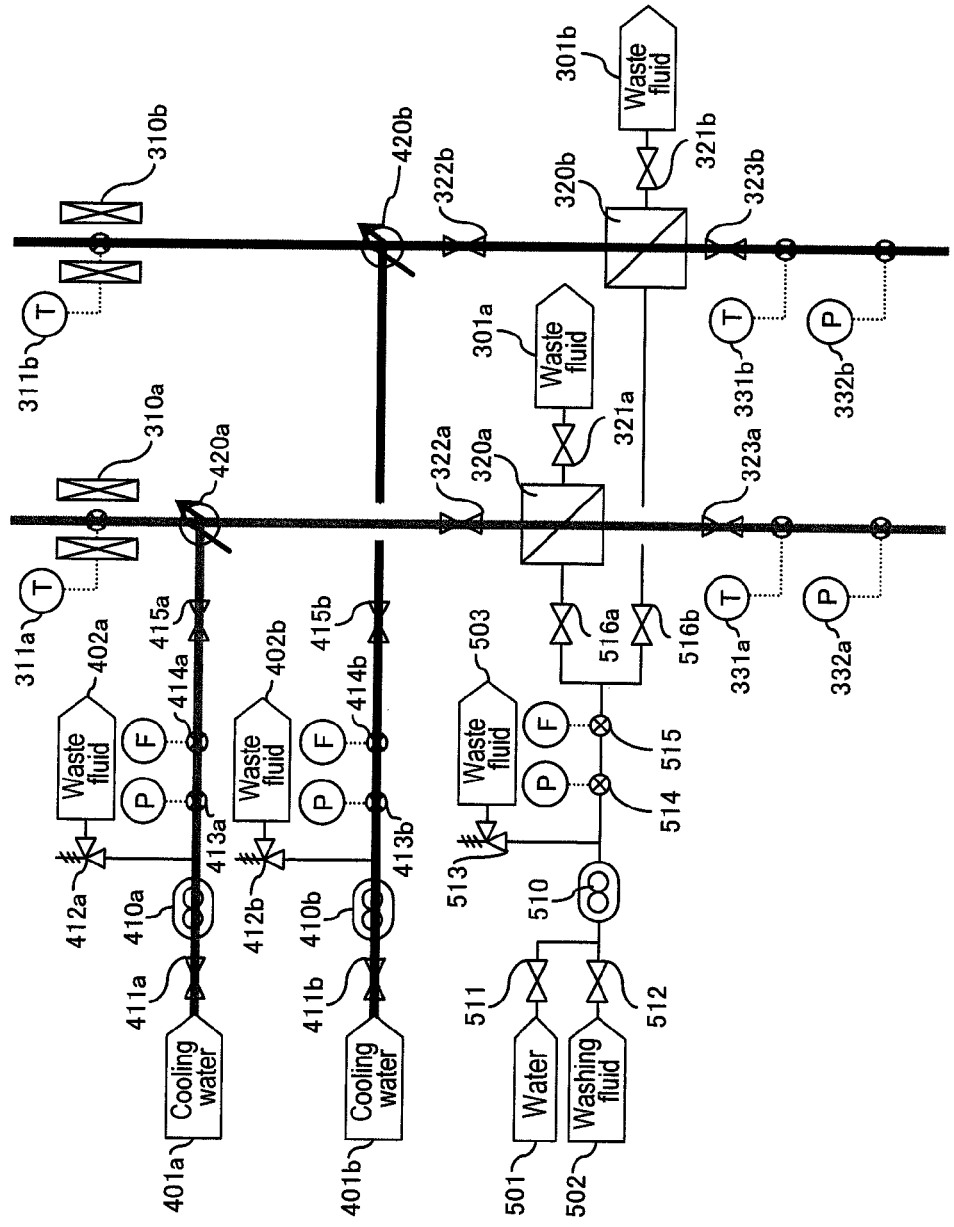
Figures 3, 12:
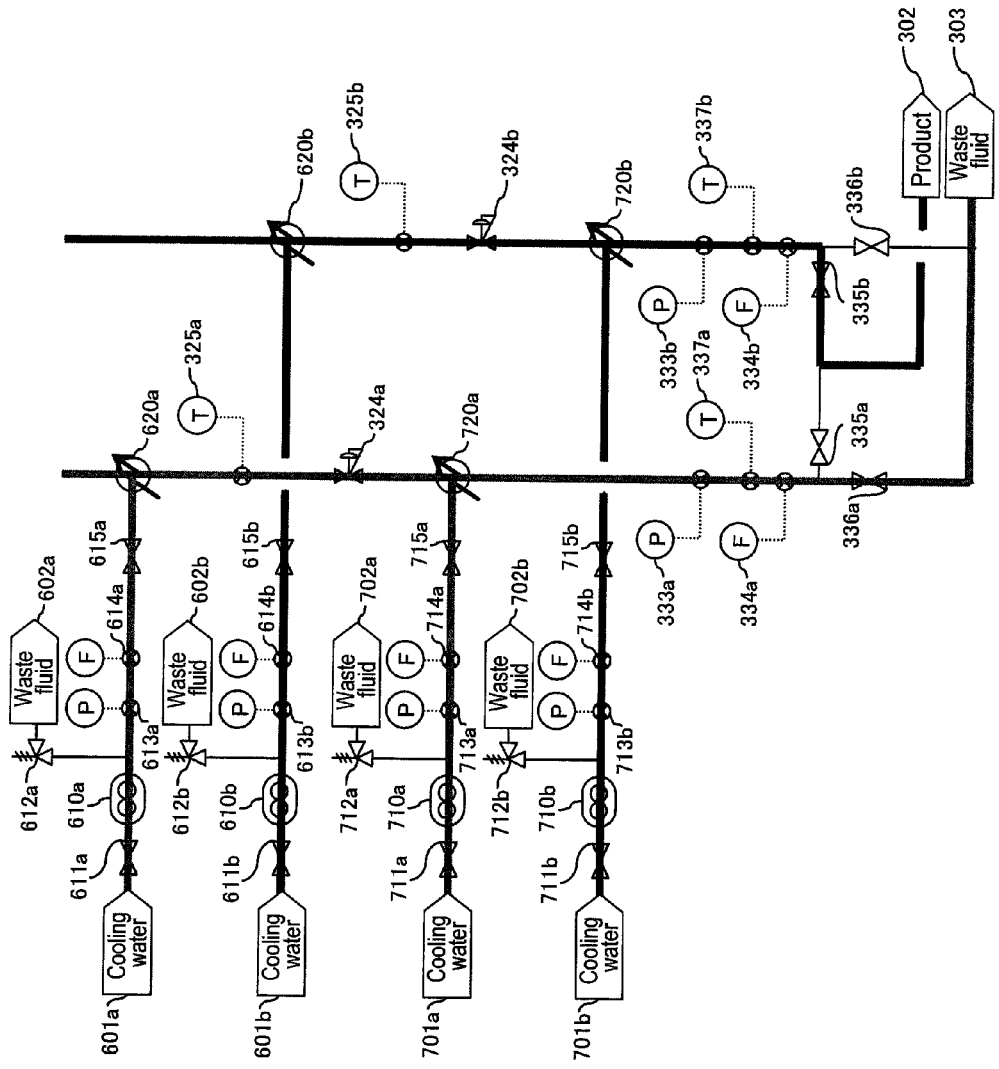
Figures 1, 13:
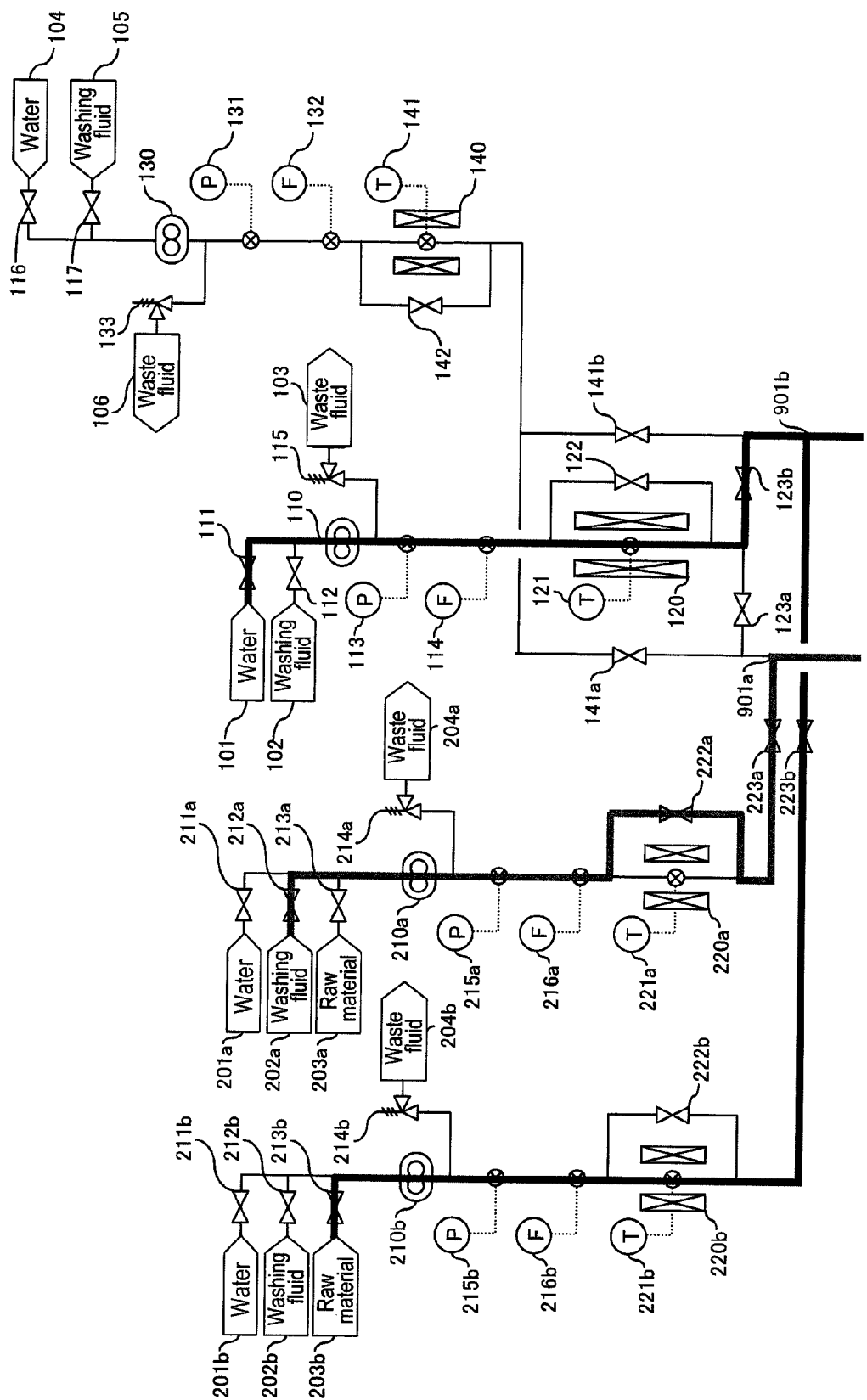
Figures 2, 13:
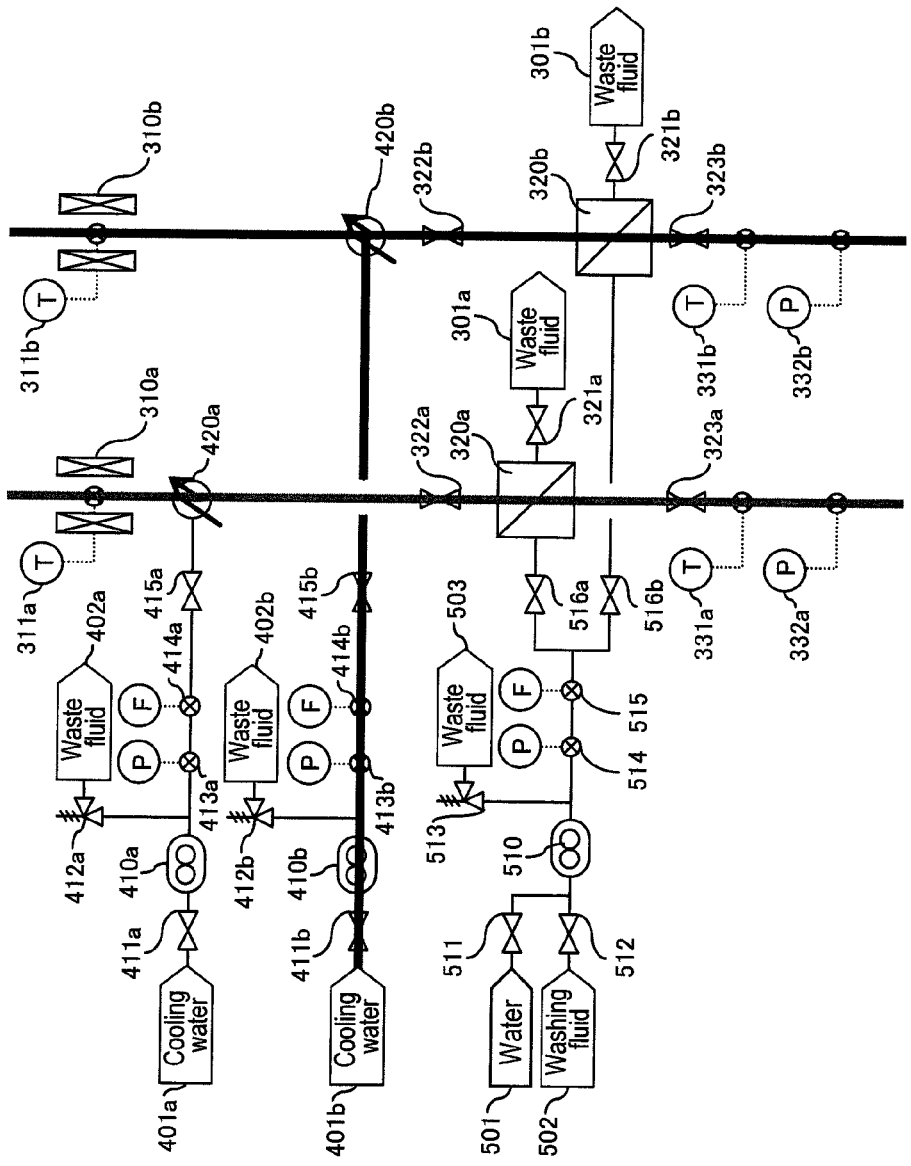
Figures 3, 13:
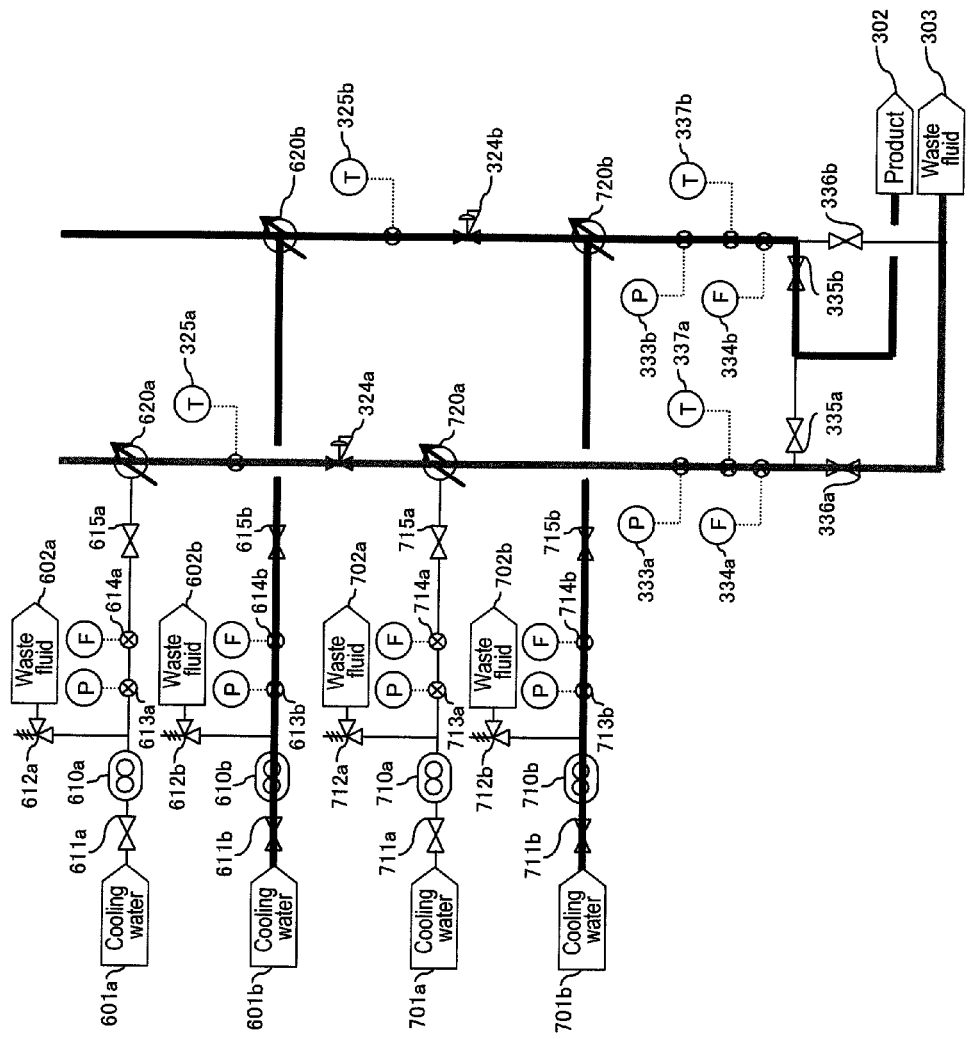

After thermometers (221a), (141) and (311a) of the preheaters (220a), (140) and the heater (310a) are lowered to predetermined temperatures, valves (222a), (142) of bypass lines of the preheaters are opened to continue the cooling of the a-system (FIG. 12). After the thermometer (311a) of the preheater is lowered to a predetermined temperature, a valve (212a) of a washing fluid header (202a) is opened and the valve (211a) of the water header (201a) is opened simultaneously, and washing of the a-system is started (FIG. 13).

Figures 1, 14:
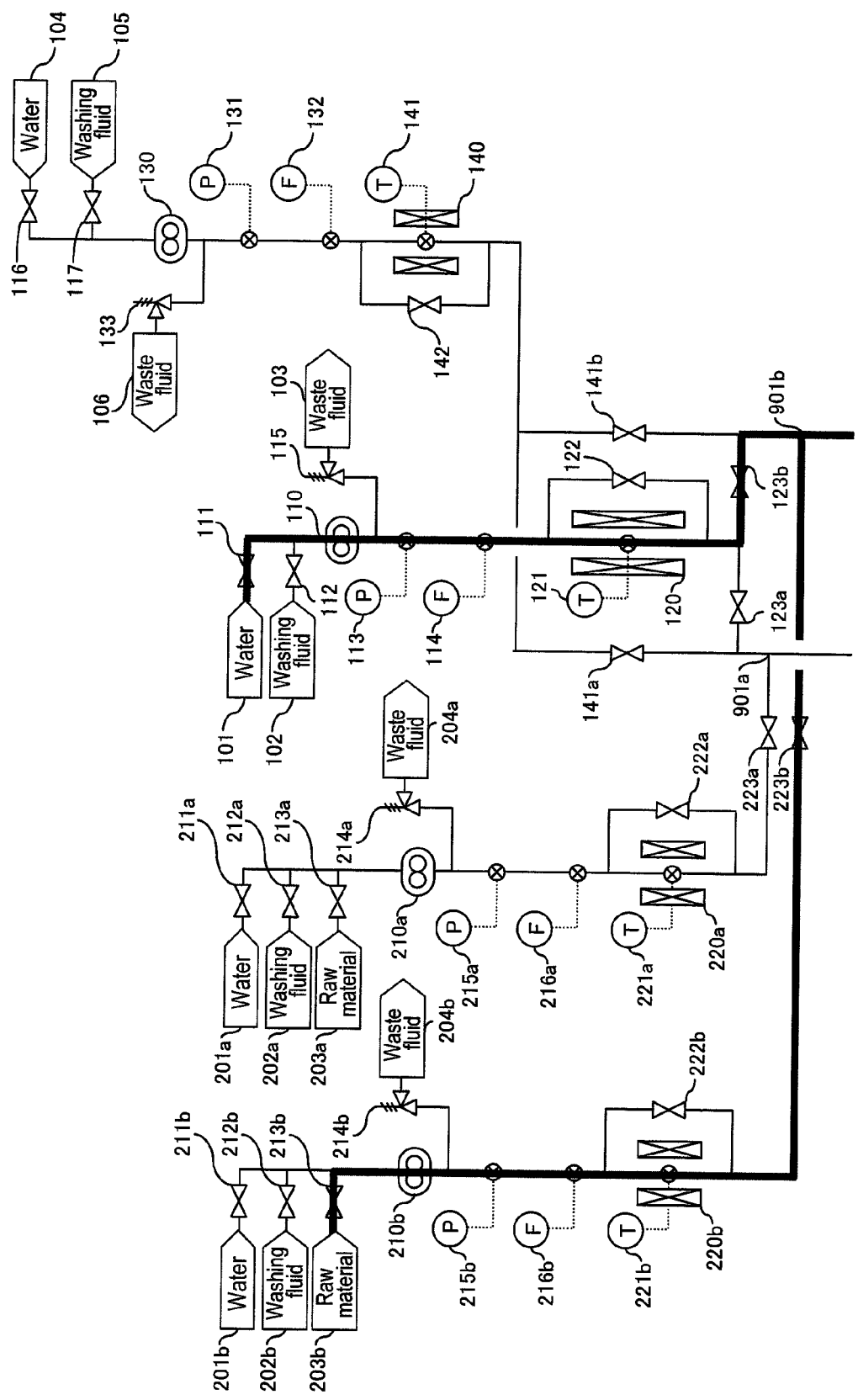
Figures 2, 14:
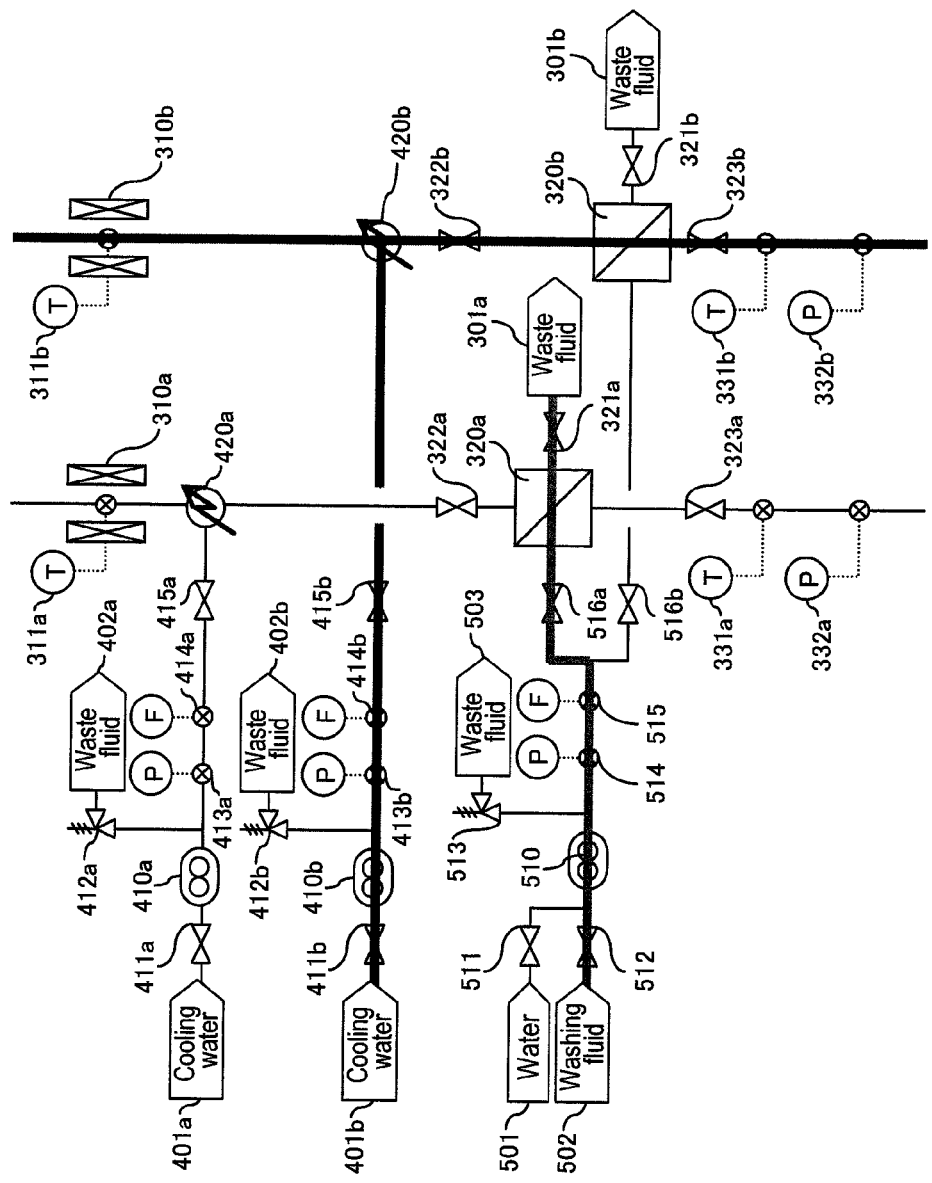
Figures 3, 14:
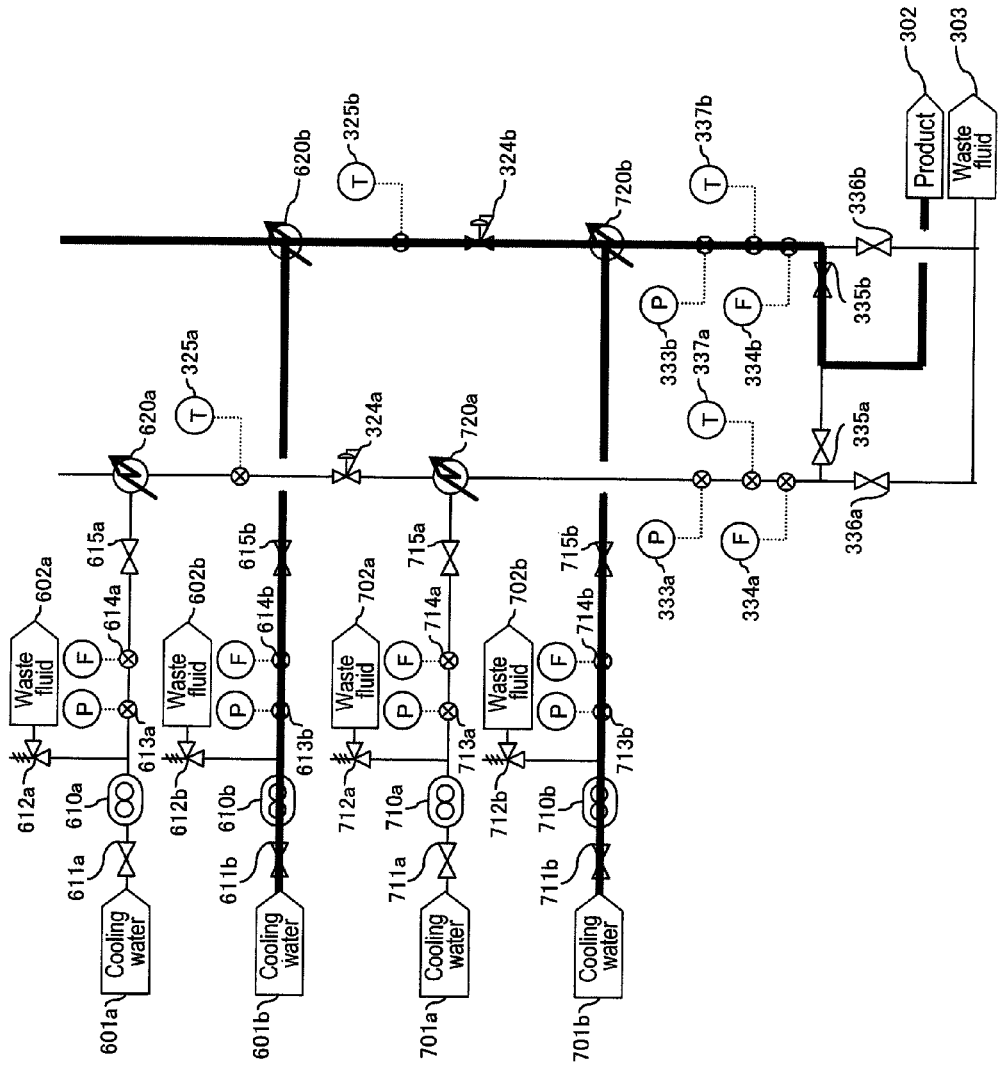
Figures 1, 15:
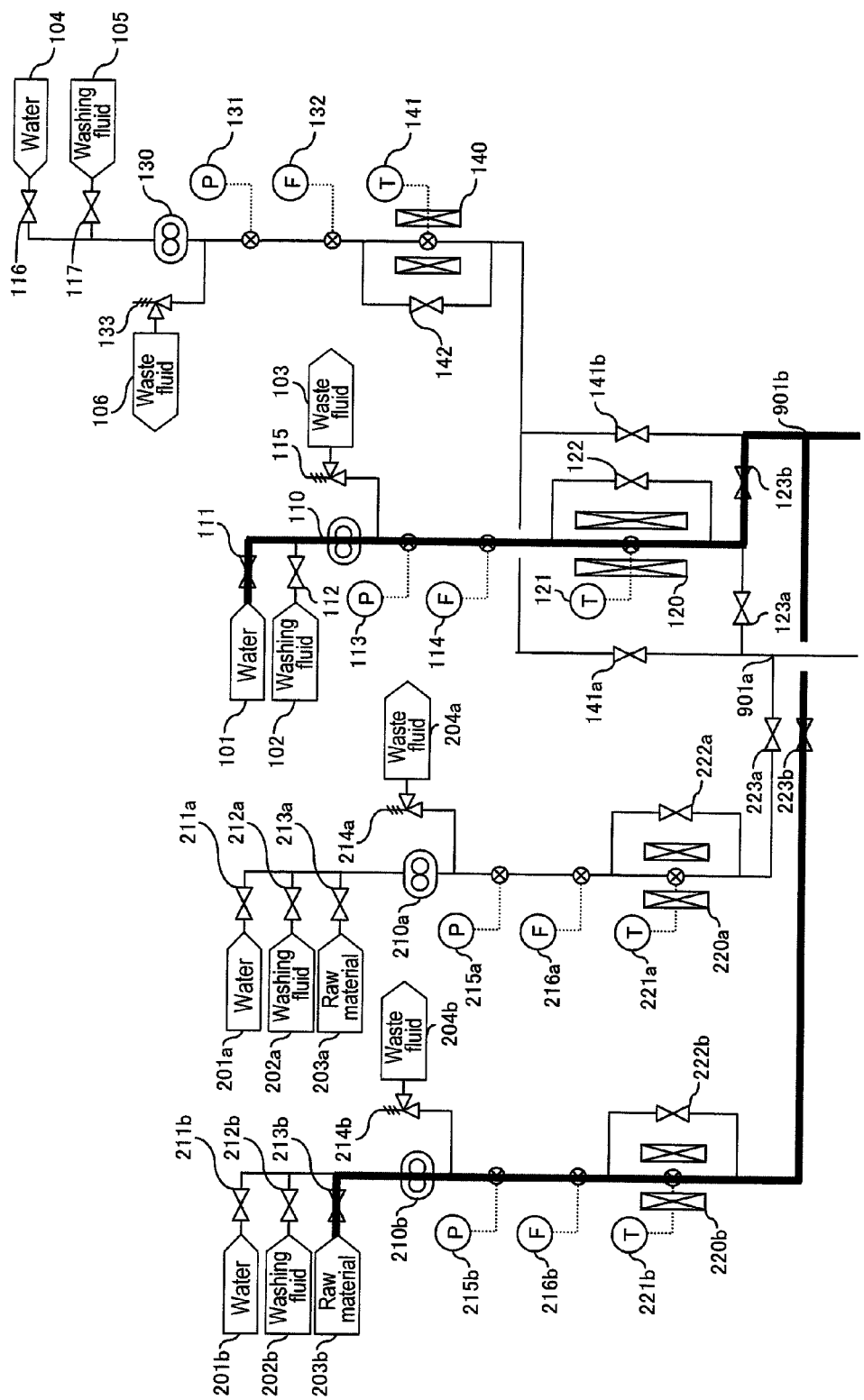
Figures 2, 15:
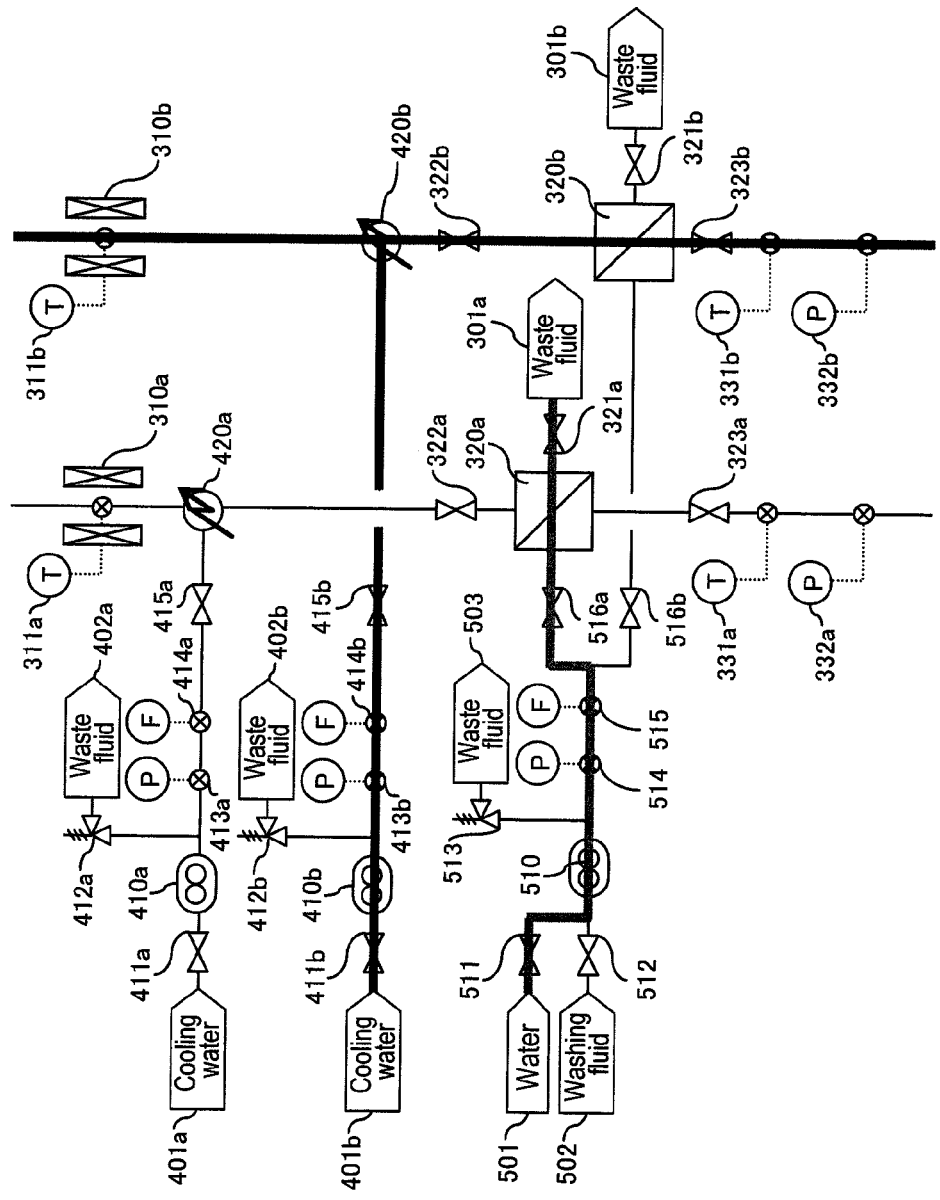
Figures 3, 15:
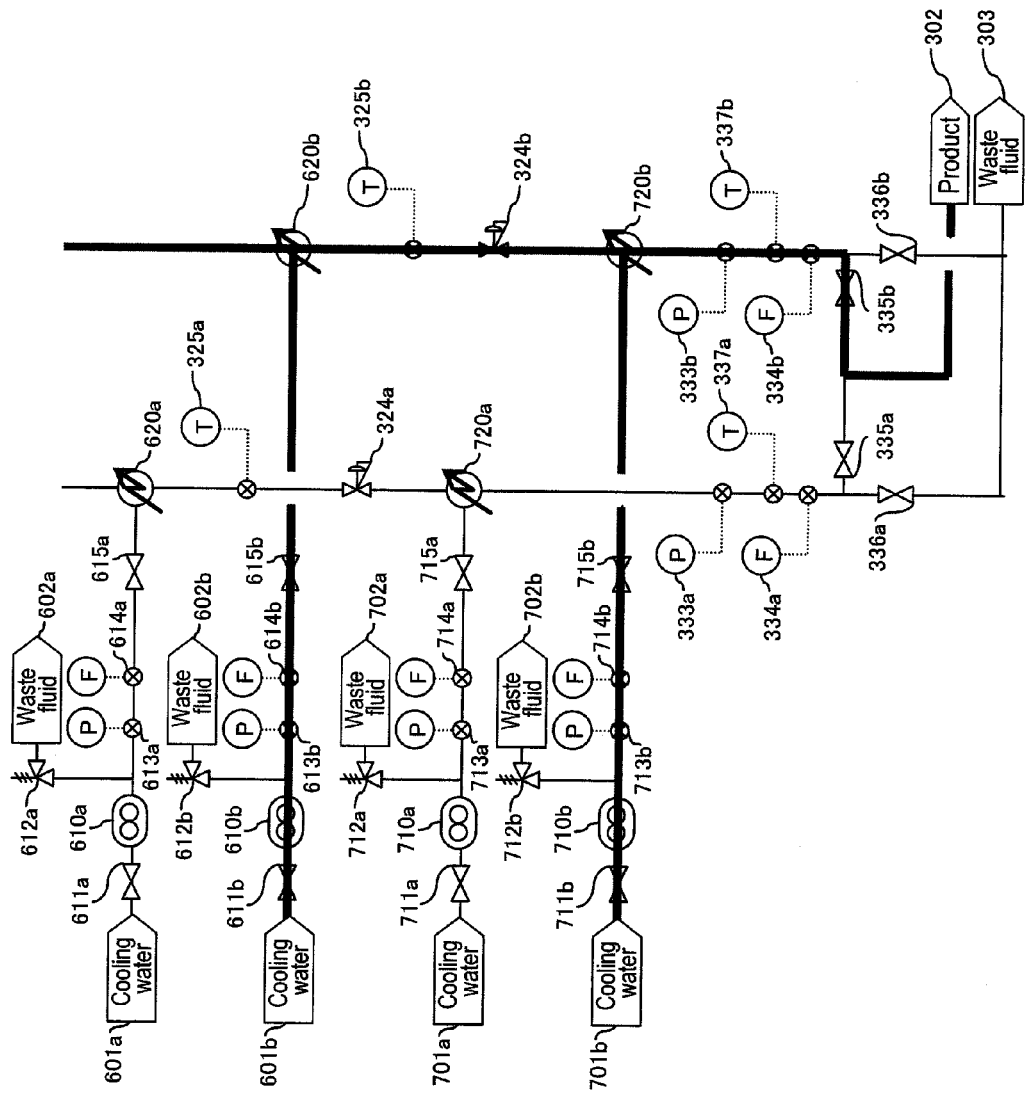
Figures 1, 16:
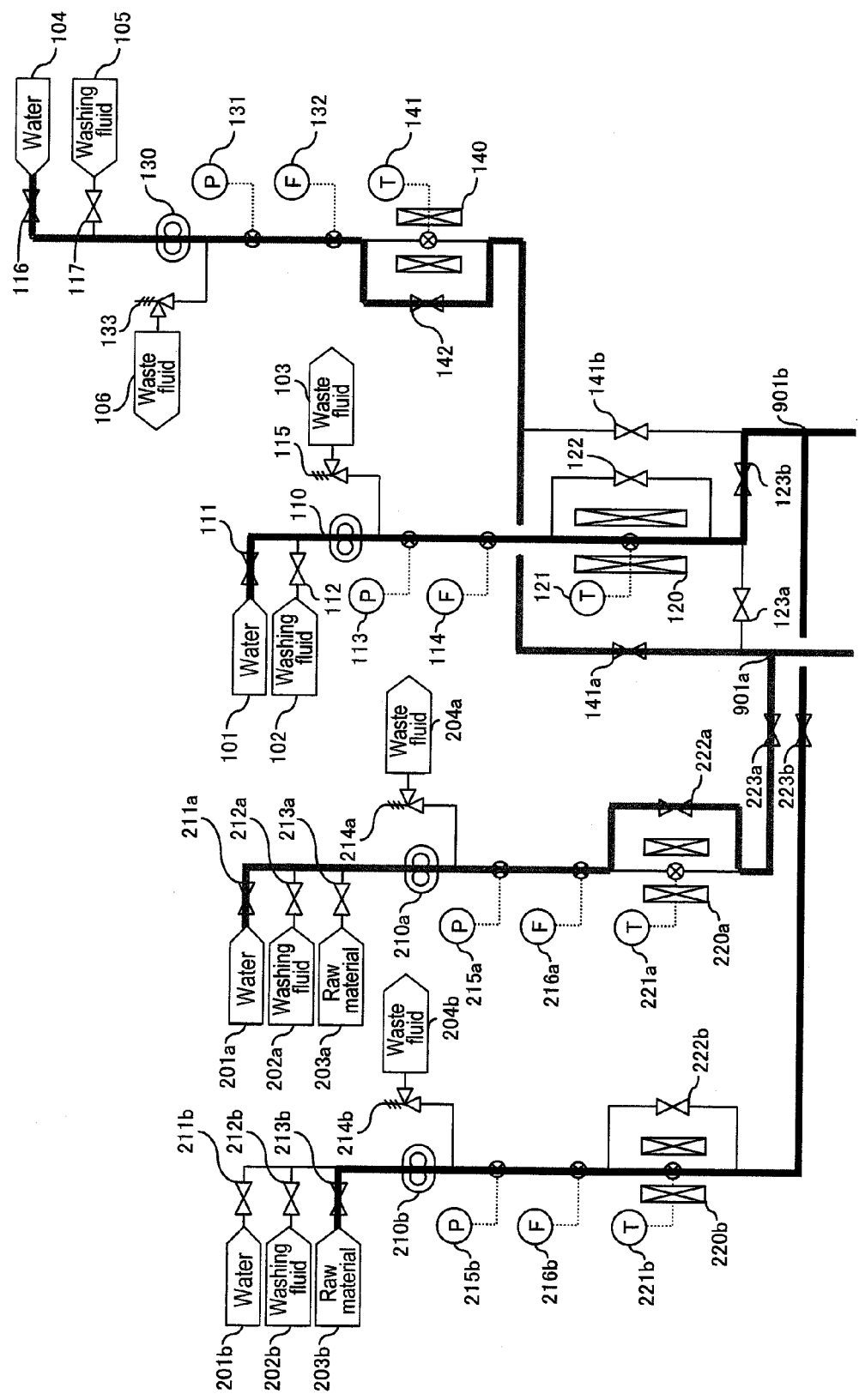
Figures 2, 16:
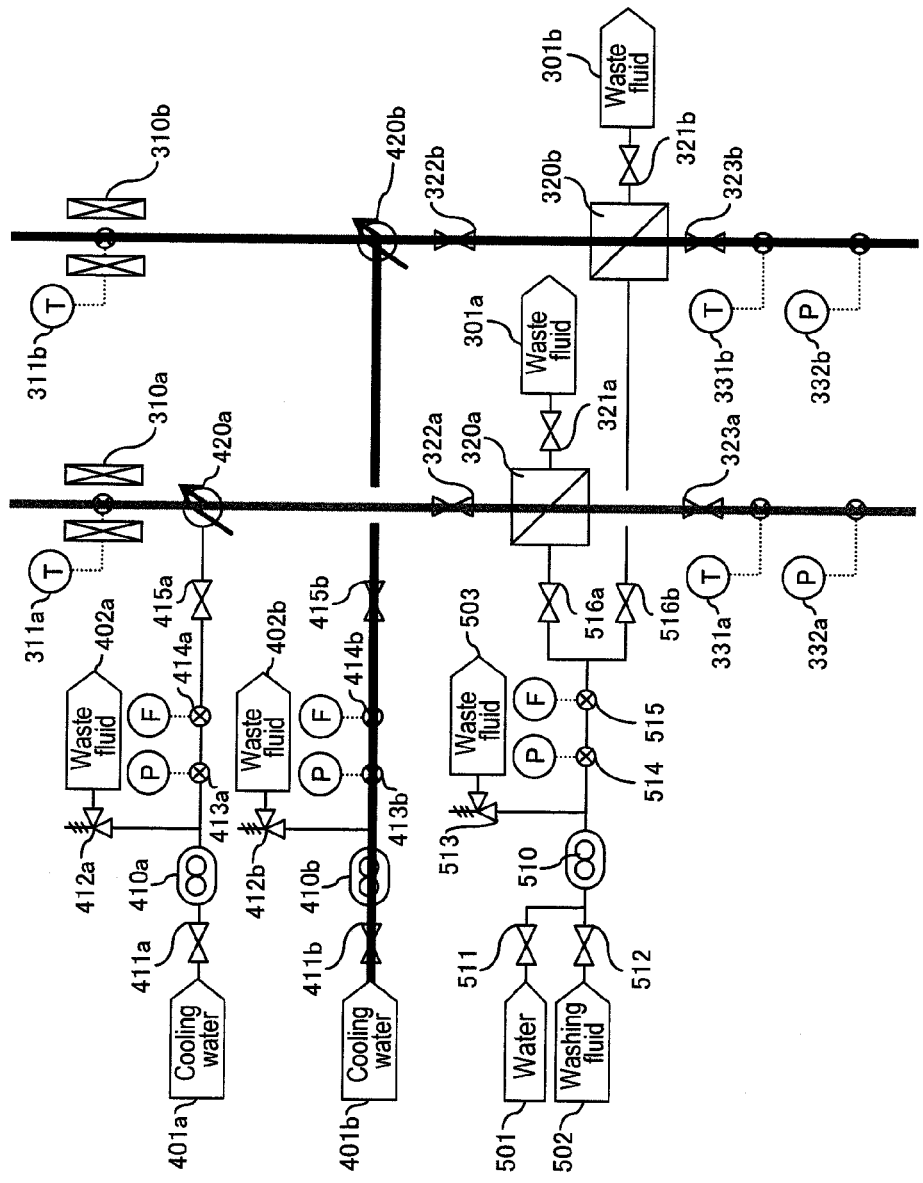
Figures 3, 16:
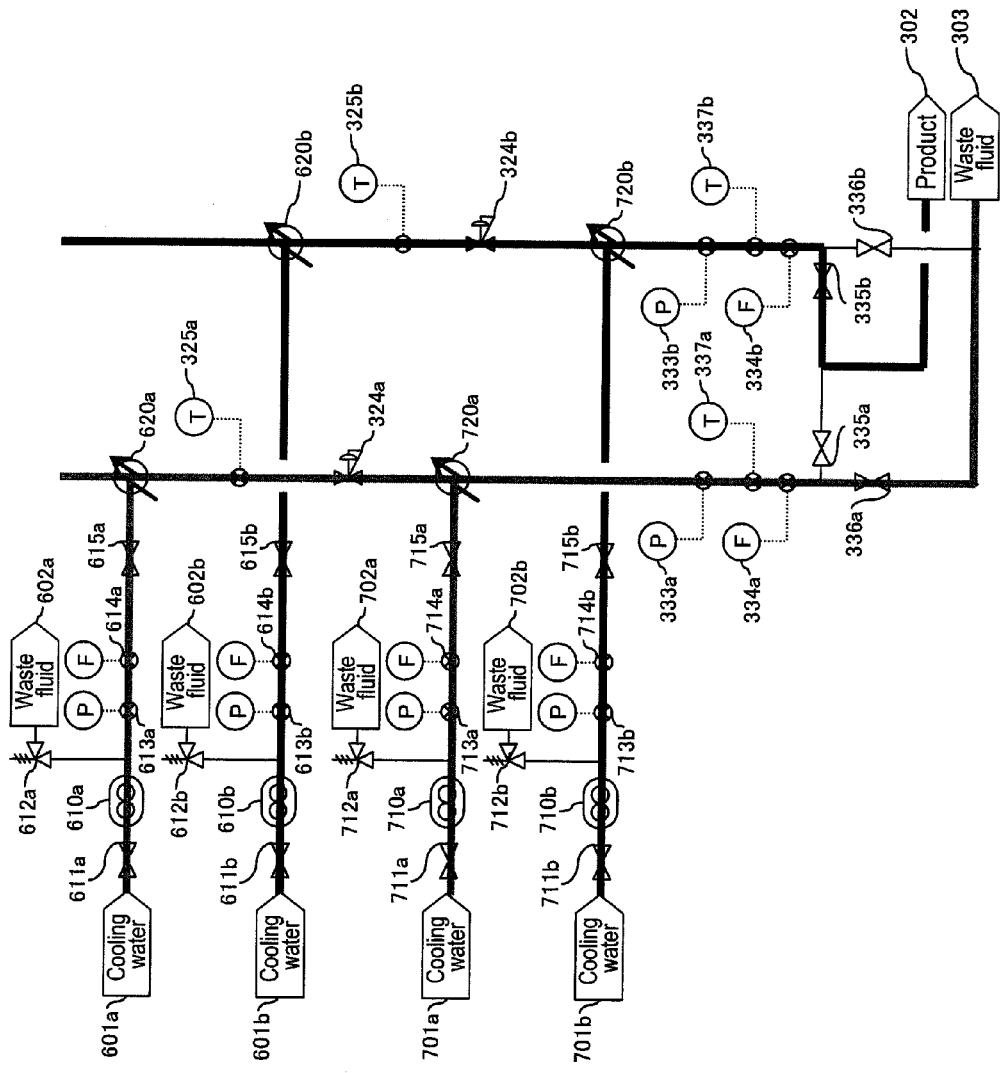
Figures 1, 17:
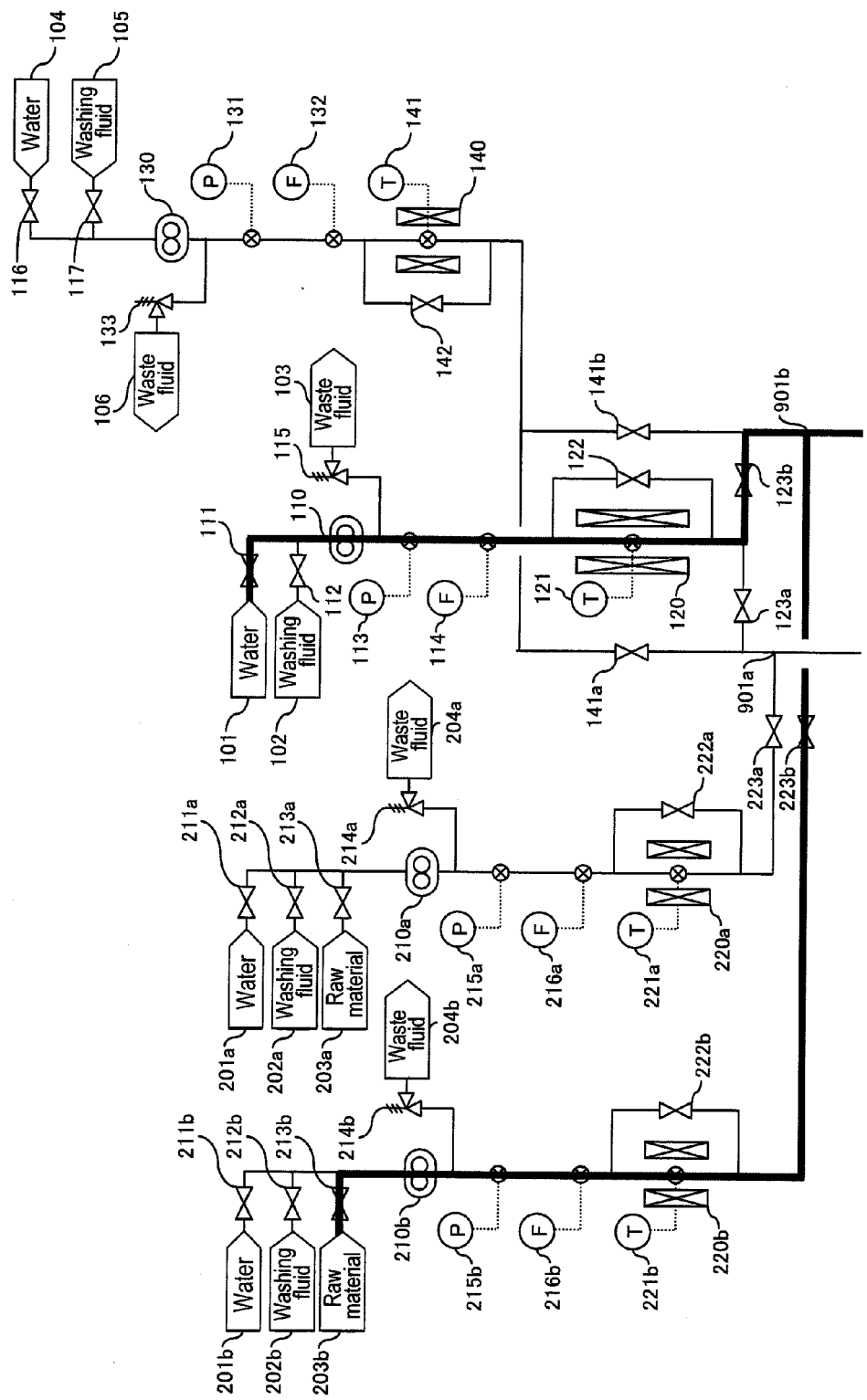
Figures 2, 17:
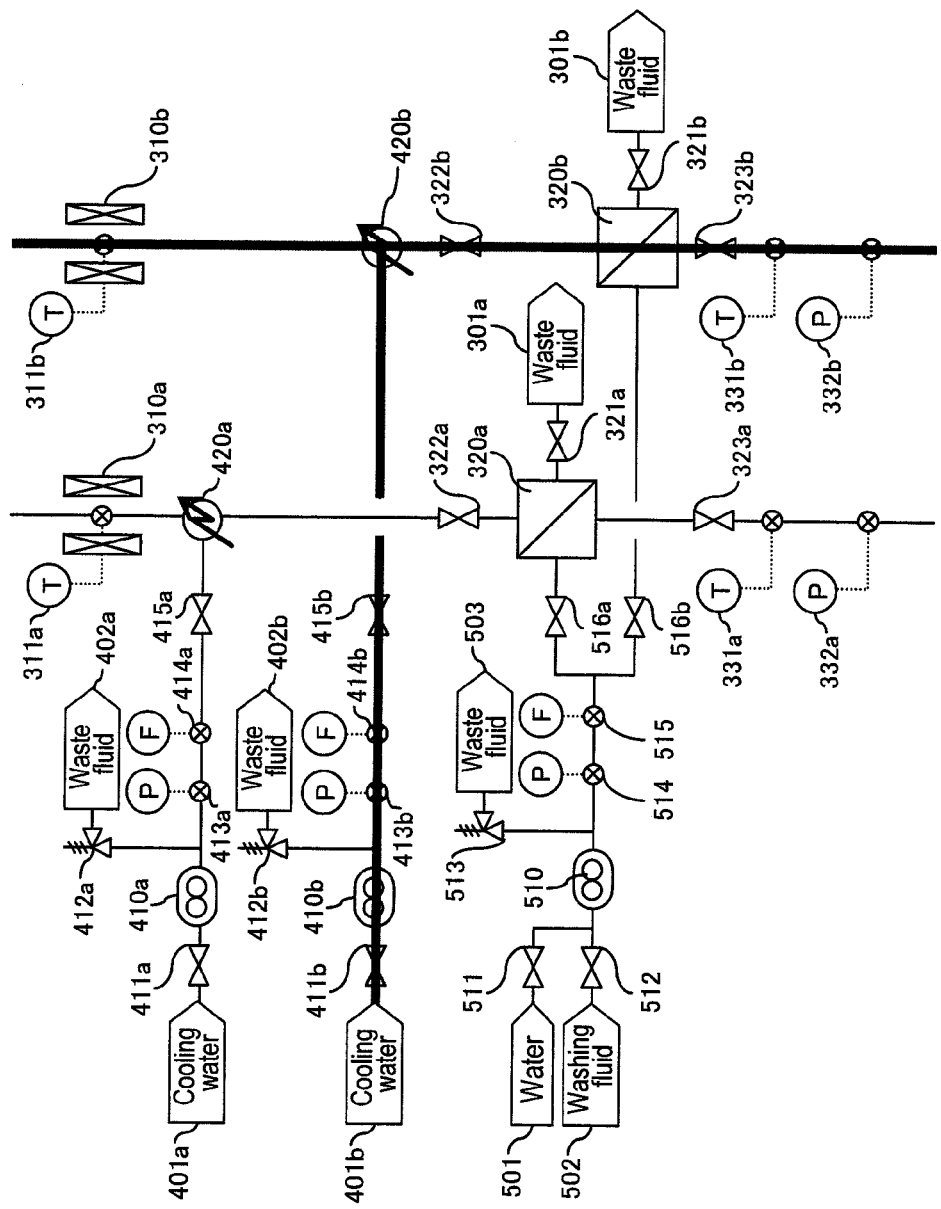
Figures 3, 17:
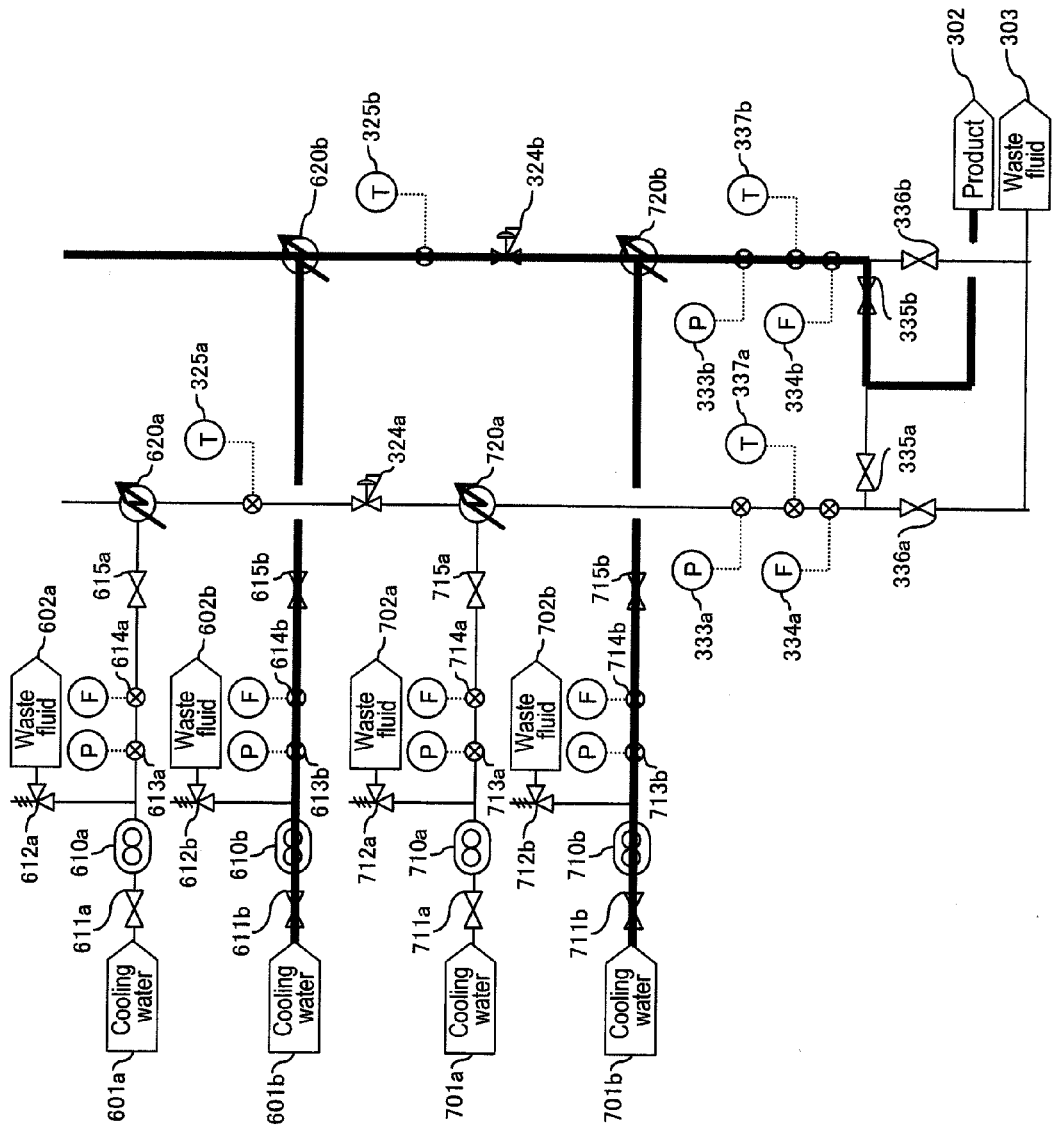

After finishing the washing of the line, the pump (210a) is stopped, the valves (322a) and (323a) are closed and the valves (512) and (516a) are opened to back-wash the filter (320a) with a washing fluid (FIG. 14). Thereafter, a valve (511) of a water header (501) is opened and the valve (512) for the washing fluid (502) is closed to back-wash the filter (320a) with water (FIG. 15). Next, the a-system line is washed with water (FIG. 16). Thereafter the pump is stopped (FIG. 17). When a differential pressure between a pressure gauge (215b) or (113) and the pressure gauge (332b) exceeds a predetermined value, that is, when a sign for the blockage at a filter or a hydrocyclone (320b) due to a by-product of the reaction mainly including carbon particles is shown, the a-system is reactivated similarly to the above, and continuous production is performed.

EXAMPLE 2

With the method of Example 1, a continuous synthesis experiment for acrolein was performed for about 2 hours in a glove box including local ventilation provided with ventilation equipment using activated carbon under the conditions of raw-material glycerin concentration of 15 wt %, reaction temperature at 400° C., reaction pressure at 35 MPa, and reaction time of 2 s (seconds). As a result, in the obtained reaction solution, the yield of acrolein was 70%, the yield of solution generated by heat decomposition of tar or the like was 20%, and the yield of carbon particles was 10%.

The solution generated by heat decomposition of tar or the like was molecules with a carbon number of 10 to 50 by GC analysis, having the melting viscosity of 300, 10, 1 and 0.1 Pa·s or less at 70, 80, 90 and 100° C., respectively. In this experiment, the reaction solution was mixed with cooling water of substantially the same volume to lower the temperature to about 200° C. The resultant was then allowed to pass through a 3-μm filter produced by Swagelok. Then, any problems did not arise because during passage through the filter, the filter differential pressure did not rise and after the completion of the experiment, no solid matter and tar adhered were observed at the filter surface. In this experiment, carbon particles of about 10 μm in diameter were separated for removal with the efficiency of 95%.

In this experiment, the following operation was further preformed. The reaction solution subjected to the carbon-particle removal was allowed to flow in a double tube of 1 m in length for indirect cooling by cooling water, thus lowering the temperature of the reaction solution to 80° C. Thereafter, pressure was reduced to 5 MPa or lower by a pressure-reducing valve.

After finishing the experiment, no solid matter nor tar adhered were observed inside the double tube and the pressure-reducing valve. Further, in this experiment, the reaction solution was allowed to flow through the double tube for indirect cooling by cooling water until the temperature of the reaction solution became at 53° C., and then the reaction solution was discharged from the system. Thereby, vapors containing small amount of entrained water was generated in acrolein, which was then allowed to condense, whereby a high-concentration acrolein aqueous solution was captured.

COMPARATIVE EXAMPLE

An acrolein synthesis experiment was performed in a similar manner to Example 2, where the reaction solution was allowed to flow through a double tube of 2 m in length for indirect cooling by cooling water until the temperature of the reaction solution was lowered to 20° C. Thereafter, the reaction solution was allowed to pass through a 3-μm filter produced by Swagelok, and pressure was reduced to 5 MPa or lower by a pressure-reducing valve. As a result, the filter differential pressure rose in the operation for about 10 minutes, and so the experiment was stopped. After finishing the experiment, a by-product on the order of several mm in particle diameter adhered to a filter surface. When the by-product was collected and washed with acetone, the particles were separated into carbon particles of 10 μm in diameter.

Description of Reference Numbers
101 Water header
106 Waste fluid line
110 High-pressure pump
120 Preheater
201, 201a, b Water header
203, 203a, b Acid header
203', 203a', b' Raw material header
204a, b Waste fluid line
210a, b High-pressure pump
214a, b Safety valve
220, 220a, b Preheater
302 Product capture line
303 Waste fluid line
310, 310a, b Heater
320, 320a, b Filter (or hydrocyclone)
324, 324a, b Pressure-reducing valve (pressure-regulating valve)
401a, b Cooling water header
402a, b Waste fluid line
410a, b High-pressure pump
412a, b Safety valve
420a, b First cooler (cooling water direct mixing type)
601a, b Cooling water header
620, 620a, b Second cooler
701, 701a, b Cooling water header
7210, 720a, b Third cooler
901, 901a, b Raw material•supercritical water junction

The invention claimed is:

1. A method for synthesizing organic matter comprising the steps of:
cooling a reaction solution to 100 to 200° C. by first cooling, the reaction solution being obtained through action of supercritical water and acid with an organic compound raw material;
separating, from the reaction solution, a solid component included in the reaction solution for removal; and
then after cooling the reaction solution to a temperature of about 100° C. or lower by second cooling, reducing pressure.

2. The method for synthesizing organic matter according to claim 1, wherein after reducing pressure, the reaction solution undergoes third cooling.

3. The method for synthesizing organic matter according to claim 1, wherein, in the first cooling, cooling water is directly mixed with the reaction solution for cooling.

4. The method for synthesizing organic matter according to claim 2, wherein the reaction solution after the first cooling includes a material with viscosity of about 0.1 Pa·s or less, the reaction solution after the second cooling includes a material with viscosity of about 10 Pa·s or less, and the reaction solution is cooled by the third cooling to a temperature of a boiling point of a target reaction material or higher.

5. The method for synthesizing organic matter according to claim 2, wherein a temperature in the third cooling is about 53° C. or higher.

6. The method for synthesizing organic matter according to claim 1, wherein process from reaction to separation for removal is performed in a vertical pipe separated by a valve.

7. The method for synthesizing organic matter according to claim 1, wherein process from reaction to separation for removal is performed in a plurality of systems of vertical pipes each separated by a valve.

8. The method for synthesizing organic matter according to claim 1, wherein the organic compound raw material comprises glycerin and the target reaction material comprises acrolein.

9. An apparatus that synthesizes organic matter, comprising a reactor including: a high-pressure pump for feeding at least water; a preheater for heating the fed water to generate supercritical water; a high-pressure pump for feeding a mixed solution with an organic compound raw material and acid; a preheater for pre-heating the fed mixed solution; a heater for keeping a reaction solution at a reaction temperature, the reaction solution being obtained by mixing the supercritical water with the mixed solution; and a pressure-reducing valve, wherein
along a flow path of the reaction solution, a first cooler, a separation and removal device for solid matters, a second cooler, and a pressure-reducing valve are provided in this order to allow the reaction solution to pass therethrough and be discharged.

10. The apparatus that synthesizes organic matter according to claim 9, wherein a plurality of systems, each including the first cooler, the separation and removal device for solid matter, the second cooler, and the pressure-reducing valve, are provided in parallel.

11. The method for synthesizing organic matter according to claim 2, wherein, in the first cooling, cooling water is directly mixed with the reaction solution for cooling.

12. The method for synthesizing organic matter according to claim 11, wherein the reaction solution after the first cooling includes a material with viscosity of about 0.1 Pa·s or less, the reaction solution after the second cooling includes a material with viscosity of about 10 Pa·s or less, and the reaction solution is cooled by the third cooling to a temperature of a boiling point of a target reaction material or higher.

13. The method for synthesizing organic matter according to claim 3, wherein the reaction solution after the first cooling includes a material with viscosity of about 0.1 Pa·s or less, the reaction solution after the second cooling includes a material with viscosity of about 10 Pa·s or less, and the reaction solution is cooled by the third cooling to a temperature of a boiling point of a target reaction material or higher.

14. The method for synthesizing organic matter according to claim 3, wherein a temperature in the third cooling is about 53° C. or higher.

15. The method for synthesizing organic matter according to claim 4, wherein a temperature in the third cooling is about 53° C. or higher.

16. The method for synthesizing organic matter according to claim 11, wherein a temperature in the third cooling is about 53° C. or higher.

17. The method for synthesizing organic matter according to claim 2, wherein process from reaction to separation for removal is performed in a vertical pipe separated by a valve.

18. The method for synthesizing organic matter according to claim 3, wherein process from reaction to separation for removal is performed in a vertical pipe separated by a valve.

19. The method for synthesizing organic matter according to claim 4, wherein process from reaction to separation for removal is performed in a vertical pipe separated by a valve.

20. The method for synthesizing organic matter according to claim 5, wherein process from reaction to separation for removal is performed in a vertical pipe separated by a valve.

21. The method for synthesizing organic matter according to claim 2, wherein process from reaction to separation for removal is performed in a plurality of systems of vertical pipes each separated by a valve.

22. The method for synthesizing organic matter according to claim 3, wherein process from reaction to separation for removal is performed in a plurality of systems of vertical pipes each separated by a valve.

23. The method for synthesizing organic matter according to claim 4, wherein process from reaction to separation for removal is performed in a plurality of systems of vertical pipes each separated by a valve.

24. The method for synthesizing organic matter according to claim 5, wherein process from reaction to separation for removal is performed in a plurality of systems of vertical pipes each separated by a valve.

25. The method for synthesizing organic matter according to claim 2, wherein the organic compound raw material comprises glycerin and the target reaction material comprises acrolein.

26. The method for synthesizing organic matter according to claim 3, wherein the organic compound raw material comprises glycerin and the target reaction material comprises acrolein.

27. The method for synthesizing organic matter according to claim 4, wherein the organic compound raw material comprises glycerin and the target reaction material comprises acrolein.

28. The method for synthesizing organic matter according to claim 5, wherein the organic compound raw material comprises glycerin and the target reaction material comprises acrolein.

29. The method for synthesizing organic matter according to claim 6, wherein the organic compound raw material comprises glycerin and the target reaction material comprises acrolein.

30. The method for synthesizing organic matter according to claim 7, wherein the organic compound raw material comprises glycerin and the target reaction material comprises acrolein.

31. The apparatus that synthesizes organic matter according to claim 9, wherein the first cooler is configured to cool the reaction solution to a temperature of 100 to 200° C., and the second cooler is configured to cool the reaction solution to a temperature of about 100° C. or lower.

* * * * *